(12) United States Patent
Araldi et al.

(10) Patent No.: US 7,897,595 B2
(45) Date of Patent: Mar. 1, 2011

(54) PYRIDOAZEPINE DERIVATIVES

(75) Inventors: Gian-Luca Araldi, East Setauket, NY (US); Alexander Bischoff, Smithtown, NY (US); Nhut K. Diep, Hauppauge, NY (US)

(73) Assignee: Forest Laboratories Holdings Limited (BM)

( * ) Notice: Subject to any disclaimer, the term of this patent is extended or adjusted under 35 U.S.C. 154(b) by 723 days.

(21) Appl. No.: 11/752,683

(22) Filed: May 23, 2007

(65) Prior Publication Data

US 2007/0281918 A1    Dec. 6, 2007

Related U.S. Application Data

(60) Provisional application No. 60/808,628, filed on May 26, 2006.

(51) Int. Cl.
*A61P 3/00*    (2006.01)
*A61K 31/55*   (2006.01)
*C07D 487/04*  (2006.01)

(52) U.S. Cl. .................... 514/212.06; 514/215; 540/521; 540/578; 540/580

(58) Field of Classification Search ............. 514/212.06, 514/215; 540/521, 578, 580
See application file for complete search history.

(56) References Cited

U.S. PATENT DOCUMENTS

| 3,987,047 | A  | 10/1976 | Griss et al. |
| 4,409,220 | A  | 10/1983 | Hurnaus et al. |
| 6,953,787 | B2 | 10/2005 | Smith et al. |
| 2007/0060568 | A1 | 3/2007 | Smith et al. |
| 2007/0191259 | A1 | 8/2007 | Aiwerx et al. |

FOREIGN PATENT DOCUMENTS

| DE | 2357253       | 5/1975  |
| DE | 2442097       | 3/1976  |
| DE | 2521544       | 12/1976 |
| DE | 2617101       | 11/1977 |
| DE | 2638828       | 3/1978  |
| DE | 2722416       | 11/1978 |
| WO | WO 97/48702   | 12/1997 |
| WO | WO 03/057213  | 7/2003  |
| WO | WO 03/086306  | 10/2003 |
| WO | WO 03/095428  | 11/2003 |
| WO | WO 2004/031181 | 4/2004 |
| WO | WO 2005/003096 | 1/2005 |
| WO | WO 2005/019179 | 3/2005 |
| WO | WO 2005/019180 | 3/2005 |
| WO | WO 2005/025576 | 3/2005 |
| WO | WO 2005/042490 | 5/2005 |
| WO | WO 2005/042491 | 5/2005 |
| WO | WO 2005/051398 | 6/2005 |
| WO | WO 2005/051399 | 6/2005 |
| WO | WO 2005/082859 | 9/2005 |
| WO | WO 2006/004931 | 1/2006 |
| WO | WO 2006/044762 | 4/2006 |
| WO | WO 2006/069363 | 6/2006 |
| WO | WO 2006/071740 | 7/2006 |
| WO | WO 2007/025144 | 3/2007 |
| WO | WO 2007/028082 | 3/2007 |
| WO | WO 2007/028083 | 3/2007 |
| WO | WO 2007/028131 | 3/2007 |
| WO | WO 2007/028132 | 3/2007 |
| WO | WO 2008/009125 | 1/2008 |

OTHER PUBLICATIONS

International Preliminary Report on Patentability for PCT/US2007/069552, mailed Dec. 11, 2008.
Glennon et al., α4β2 nACh Receptor Pharmacophore Models, 2004, Bioorg. Med. Chem. Lett., vol. 14, pp. 1841-1844.
International Search Report for PCT/US07/69552, mailed Nov. 7 2007.
Written Opinion of the International Search Authority for PCT/US07/69552, mailed Nov. 7, 2007.
Dunlop et al., Pharmacological Profile of the 5-HT$_{2c}$ Receptor Agonist WAY-163909; Therapeutic Potential in Multiple Indications. CNS Drug Reviews, 2006, vol. 12, No. 3-4, 167-177.
Garzya et al., Studies Towards the Identification of a New Generation of Atypical Antipsychotic Agents. Bioorg. & Med. Chem. Lett., 17(2007) 400-405.
Jandacek, APD-356, Curr. Op. Invest. Drugs 2005, 6(10), 1051-56.
McKenna et al., Novel Tacrine Analogues for Potential Use Against Alzheimer's Disease: Potent and Selective Acetylcholinesterase Inhibitors and 5-HT Uptake Inhibitors. J. Med. Chem. 1997, 40, 3516-3523.
Negash et al., Further Definition of the $D_1$ Dopamine Receptor Pharmacophore: Synthesis of *trans*-6,6a,7,8,9,13b-Hexahydro-5*H*-benzo[*d*]naphtha[2,1-*b*]azepines as Rigid Analogues of β-Phenyldopamine. J. Med. Chem. 1997, 49, 2140-2147.
Nilsson, 5-Hydroxytryptamine 2C (5-HT$_{2c}$) Receptor Agonists as Potential Antiobesity Agents. J. Med. Chem. Published on web Jun. 17, 2006, A-L.
Smith et al., Discovery and SAR of New Benzazepines as Potent and Selective 5-HT$_{2c}$ Receptor Agonists for the Treatment of Obesity. Bioorg. & Med. Chem. Lett., 15 (2005) 1467-1470.
Smith et al., The Potential Use of Selective 5-HT$_{2c}$ Agonists in Treating Obesity. Expert Opin. Investig. Drugs (2006) 15(3):257-266.
Weinstock et al., Synthesis, Conformation, and Dopaminergic Activity of 5,6-Ethano-bridged Derivatives of Selective Dopaminergic 3-Benzazepines. J. Med. Chem. 1987, 30, 1303-1308. ADP-356, thomsonpharma.com, Jan. 12, 2006.
Drug Report for : Locaserin, Thomson Current Drugs, IDDB3, Sep. 17, 2006.
Locaserin, thompsonpharma.com, Feb. 22, 2007.

*Primary Examiner* — Brenda L Coleman
(74) *Attorney, Agent, or Firm* — Charles Ryan; Michael Ciradlo; Hemant Khanna

(57) ABSTRACT

The present invention relates to pyridoazepine derivatives that act as 5-HT ligands, e.g., 5-HT$_2$ C. The invention also relates to methods of preparing the compounds, compositions containing the compounds, and to methods of treatment using the compounds.

29 Claims, No Drawings

PYRIDOAZEPINE DERIVATIVES

This application claims the benefit of U.S. Provisional Application Ser. No. 60/808,628, filed May 26, 2006, the entire disclosure of which is hereby incorporated by reference.

FIELD OF THE INVENTION

The present invention relates to pyridoazepine derivatives that act as 5-HT ligands, e.g., 5-HT$_2$C ligands. The invention also relates to methods of preparing the compounds, compositions containing the compounds, and to methods of treatment using the compounds.

BACKGROUND OF THE INVENTION

The class of compounds known as pyridoazepines have been identified as biologically active and useful in the treatment of various physiological disorders. (see, e.g., U.S. Pat. Nos. 4,177,275 and 4,936,121 and Yamamoto et al, *Heterocycles*, 11, 267-73, 1978). For example, pyridoazepine compounds have been shown to have antihistamine and antiserotonin activity.

Serotonin (5-hydroxytryptamine or 5-HT) is a monoamine neurotransmitter synthesized in serotonergic neurons in the central nervous system and enterochromaffin cells of the gastrointestinal tract. The most common drug therapies involving 5-HT include SSRIs (serotonin reuptake inhibitors), MAOIs (monoamine oxidase inhibitors) and tricyclic antidepressants. SSRIs, considered the safest of the therapies, still possesses potential side effects including insomnia, nausea, diminished sexual interest and weight gain. (see, e.g., Hirschfeld, R., *J. Clin. Psychiatry*, 64 [suppl 18], 20-24, 2003).

Serotonin (5-HT) neurotransmission plays an important role in numerous physiological processes both in health and in psychiatric disorders. 5-HT has been implicated in the regulation of feeding behavior for some time. 5-HT appears to work by inducing a feeling of fullness or satiety so eating stops earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor ligand (e.g., a 5-HT$_{2C}$ receptor agonist) can be a more effective and safe anti-obesity agent. Also, 5-HT$_{2C}$ knockout mice are overweight with cognitive impairment and susceptibility to seizure.

It is believed that 5-HT$_{2C}$ may play a role in obsessive compulsive disorder, some forms of depression, and epilepsy. Accordingly, 5-HT$_{2C}$ receptor ligands (e.g., 5-HT$_{2C}$ receptor agonists) can have anti-panic properties, and properties useful for the treatment of sexual dysfunction.

In sum, the 5-HT$_{2C}$ receptor is a validated and well-accepted receptor target for the treatment of obesity and psychiatric disorders, and it can be seen that there is a need for selective 5-HT$_{2C}$ receptor ligands (e.g., 5-HT$_{2C}$ receptor agonists) which safely decrease food intake and body weight.

SUMMARY OF THE INVENTION

The present invention relates to pyridoazepine derivatives that act as 5-HT ligands, e.g., 5-HT$_{2C}$ ligands. The invention also relates to methods of preparing the compounds, compositions containing the compounds, and to methods of treatment using the compounds.

DETAILED DESCRIPTION OF THE INVENTION

The present invention includes compounds of formula I:

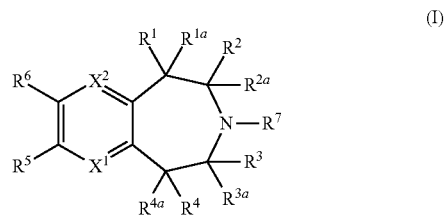

wherein $R^1$, $R^{1a}$, $R^4$ and $R^{4a}$ are each independently hydrogen, hydroxyl, alkyl, alkenyl, aryl, alkoxy, aryloxy, amino, alkylamino or arylamino;

$R^2$, $R^{2a}$, $R^3$ and $R^{3a}$ are each independently hydrogen or alkyl;

or $R^1$ and $R^{1a}$ or $R^2$ and $R^{2a}$ or $R^3$ and $R^{3a}$ or $R^4$ and $R^{4a}$, together with the carbon atom to which they are attached, independently form a C=O or C=CRR' group where R and R' are independently hydrogen or alkyl;

$R^5$ and $R^6$ are each independently hydrogen, halogen, hydroxyl, alkyl, alkenyl, aryl, arylalkyl, alkoxy, alkenyloxy, aryloxy, nitro, amino, alkylamino, dialkylamino, arylamino, diarylamino or —C(O)OR$^8$ in which R$^8$ is hydrogen, alkyl or aryl, or $R^5$ and $R^6$ together with the carbon atoms to which they are attached form a cyclic ring other than phenyl or pyridyl;

$R^7$ is hydrogen, alkyl, aryl, —C(O)R$^9$, —C(O)OR$^9$, —C(O)NR$^9$R$^{10}$, —S(O)$_2$R$^{11}$ or —S(O)R$^{11}$, in which R$^9$ and R$^{10}$ are each independently hydrogen, halogen, alkyl or aryl and R$^{11}$ is alkyl or aryl;

$X^1$ and $X^2$ are independently N, NR$^{12}$ or CR$^{12}$ in which R$^{12}$ is hydrogen, halogen, hydroxyl, alkoxy, alkyl, or alkenyl, with the provisio that at least one of X$^1$ and X$^2$ is N or NR$^{12}$, and when X$^1$ is N or NR$^{12}$, then X$^2$ is CR$^{12}$ and when X$^2$ is N or NR$^{12}$, then X$^1$ is CR$^{12}$, and pharmaceutically acceptable salts or solvates (e.g., hydrates) thereof, or solvates of pharmaceutically acceptable salts thereof;

with the proviso that said compound is not:
6,7,8,9-tetrahydro-2,3-diphenyl-5H-Pyrido[2,3-d]azepine,
2-amino-5,6,8,9-tetrahydro-7H-Pyrido[2,3-d]azepine-7-carboxylic acid 1,1-dimethylethyl ester,
6,7,8,9-tetrahydro-5H-Pyrido[2,3-d]azepin-2-amine,
6,7,8,9-tetrahydro-4-methyl-5H-Thieno[3',2':5,6]pyrido[2,3-d]azepine,
3,5,6,7,8,9-hexahydro-10-methyl-7-propyl-2H-Thieno[2',3':5,6]pyrido[2,3-d]azepine,
7-ethyl-6,7,8,9-tetrahydro-10-methyl-5H-Thieno[2',3':5,6]pyrido[2,3-d]azepine,
6,7,8,9-tetrahydro-10-methyl-7-propyl-5H-Thieno[2',3':5,6]pyrido[2,3-d]azepine,
6,7,8,9-tetrahydro-10-(2-methylpropyl)-5H-Thiazolo[5',4':5,6]pyrido[2,3-d]azepine,
7-ethyl-2,5,6,7,8,9-hexahydro-2-oxo-1H-Pyrido[2,3-d]azepine-3-carboxamide,
3-amino-7-ethyl-1,5,6,7,8,9-hexahydro-2H-Pyrido[2,3-d]azepin-2-one, 2-chloro-7-ethyl-6,7,8,9-tetrahydro-5H-Pyrido[2,3-d]
azepin-3-amine,
7-ethyl-6,7,8,9-tetrahydro-5H-Pyrido[2,3-d]azepin-3-
amine,
5,6,8,9-tetrahydro-7H-Pyrido[2,3-d]azepine-3,7-dicarboxy-
lic acid diethyl ester,
1,2,5,6,8,9-hexahydro-2-oxo-7H-Pyrido[2,3-d]azepine-7-
carboxylic acid ethyl ester,
1,2,5,6,8,9-hexahydro-2-oxo-7H-Pyrido[2,3-d]azepine-3,7-
dicarboxylic acid diethyl ester,
4-chloro-1,2,5,6,8,9-hexahydro-2-oxo-7H-Pyrido[2,3-d]
azepine-7-carboxylic acid ethyl ester,
4-chloro-1,2,5,6,8,9-hexahydro-2-oxo-7H-Pyrido[2,3-d]
azepine-3,7-dicarboxylic acid diethyl ester,
2,4-dichloro-5,6,8,9-tetrahydro-7H-Pyrido[2,3-d]azepine-3,
7-dicarboxylic acid diethyl ester,
1,2,5,6,8,9-hexahydro-4-hydroxy-2-oxo-7H-Pyrido[2,3-d]
azepine-7-carboxylic acid ethyl ester,
1,2,5,6,8,9-hexahydro-4-hydroxy-2-oxo-7H-Pyrido[2,3-d]
azepine-3,7-dicarboxylic acid diethyl ester,
6,7,8,9-tetrahydro-10-methyl-5H-Thiazolo[5',4':5,6]pyrido
[2,3-d]azepine,
5,6,8,9-tetrahydro-10-methyl-7H-Thiazolo[5',4':5,6]pyrido
[2,3-d]azepine-7-carboxylic acid ethyl ester,
7-acetyl-6,7,8,9-tetrahydro-10-methyl-5H-Thieno[2',3':5,6]
pyrido[2,3-d]azepine,
6,7,8,9-tetrahydro-10-methyl-7-propyl-5H-Thieno[2',3':5,6]
pyrido[2,3-d]azepine,
6,7,8,9-tetrahydro-10-methyl-7-(1-oxopropyl)-5H-Thieno
[2',3':5,6]pyrido[2,3-d]azepine,
3,5,6,7,8,9-hexahydro-10-methyl-7-(1-oxopropyl)-2H-
Thieno[2',3':5,6]pyrido[2,3-d]azepine,
2,3,5,6,8,9-hexahydro-10-methyl-7H-Thieno[2',3':5,6]py-
rido[2,3-d]azepine-7-carboxylic acid ethyl ester,
3,5,6,7,8,9-hexahydro-10-methyl-2H-Thieno[2',3':5,6]py-
rido[2,3-d]azepine,
6,7,8,9-tetrahydro-10-methyl-5H-Thieno[2',3':5,6]pyrido[2,
3-d]azepine, or
5,6,8,9-tetrahydro-10-methyl-7H-Thieno[2',3':5,6]pyrido[2,
3-d]azepine-7-carboxylic acid ethyl ester.

In one embodiment, the present invention relates to compounds of formula I wherein:
$R^1$, $R^{1a}$, $R^4$ and $R^{4a}$ are each independently hydrogen, hydroxyl, alkyl, alkenyl, aryl, alkoxy, aryloxy, amino, alkylamino or arylamino;
$R^2$, $R^{2a}$, $R^3$ and $R^{3a}$ are each independently hydrogen or alkyl;
or $R^1$ and $R^{1a}$ or $R^2$ and $R^{2a}$ or $R^{3a}$ and $R^4$ or $R^4$ and $R^{4a}$, together with the carbon atom to which they are attached, independently form a C=O;
$R^5$ and $R^6$ are each independently hydrogen, halogen, hydroxyl, alkyl, alkenyl, aryl, alkoxy, alkenyloxy, aryloxy, nitro, amino, alkylamino, dialkylamino, arylamino or diarylamino,
or $R^5$ and $R^6$ together with the carbon atoms to which they are attached form a cyclic ring other than phenyl or pyridyl;
$R^7$ is hydrogen, alkyl, aryl, —C(O)OR$^9$, —C(O)NR$^9$R$^{10}$ or —S(O)$_2$R$^{11}$ in which R$^9$ and R$^{10}$ are each independently hydrogen, halogen, alkyl, or aryl and R$^{11}$ is alkyl or aryl; and
$X^1$ and $X^2$ are independently N, NR$^{12}$ or CR$^{12}$ in which R$^{12}$ is hydrogen, halogen, hydroxyl, alkyl, or alkenyl, with the provisio that at least one of $X^1$ and $X^2$ is N or NR$^{12}$, and when $X^1$ is N or NR$^{12}$, then $X^2$ is CR$^{12}$ and when $X^2$ is N or NR$^{12}$, then $X^1$ is CR$^{12}$.

In another embodiment, the present invention relates to compounds of formula I wherein:
$R^1$, $R^{1a}$, $R^4$ and $R^{4a}$ are each independently hydrogen or alkyl;
$R^2$, $R^{2a}$, $R^3$ and $R^{3a}$ are each hydrogen;
or $R^1$ and $R^{1a}$ or $R^2$ and $R^{2a}$ or $R^3$ and $R^{3a}$ or $R^4$ and $R^{4a}$, together with the carbon atom to which they are attached, independently form a C=CRR' group where R and R' are hydrogen;
$R^5$ and $R^6$ are each independently hydrogen, halogen, hydroxyl, alkyl, alkenyl, alkoxy, alkenyloxy, nitro, amino, alkylamino, dialkylamino or —C(O)OR$^8$ in which R$^8$ is alkyl,
or $R^5$ and $R^6$ together with the carbon atoms to which they are attached form a cyclic ring other than phenyl or pyridyl;
$R^7$ is hydrogen, alkyl (e.g., methyl) —C(O)R$^9$ or —C(O)OR$^9$, in which R$^9$ is alkyl; and
$X^1$ and $X^2$ are independently N, NR$^{12}$ or CR$^{12}$ in which R$^{12}$ is hydrogen, halogen, hydroxyl, alkoxy or alkyl, with the provisio that at least one of $X^1$ and $X^2$ is N or NR$^{12}$, and when $X^1$ is N or NR$^{12}$, then $X^2$ is CR$^{12}$ and when $X^2$ is N or NR$^{12}$, then $X^1$ is CR$^{12}$.

In an additional embodiment, at least one of $R^1$, $R^{1a}$, $R^2$, $R^{2a}$, $R^3$, $R^{3a}$, $R^4$ and $R^{4a}$ is other than hydrogen. For example, in one embodiment, $R^1$ is methyl and $R^{1a}$, $R^2$, $R^{2a}$, $R^3$, $R^{3a}$, $R^4$ and $R^{4a}$ are hydrogen. In another embodiment, $R^1$ and $R^3$ are methyl and $R^{1a}$, $R^2$, $R^{2a}$, $R^{3a}$, $R^4$ and $R^{4a}$ are hydrogen. In yet another embodiment, $R^4$ is methyl and $R^1$, $R^{1a}$, $R^2$, $R^{2a}$, $R^3$, $R^{3a}$ and $R^{4a}$ are hydrogen. In a further embodiment, $R^{1a}$, $R^{2a}$, $R^{3a}$ and $R^{4a}$ are hydrogen.

In a further embodiment, $R^2$, $R^{2a}$, $R^3$, $R^{3a}$, $R^4$ and $R^{4a}$ are hydrogen and $R^1$ and $R^{1a}$, together with the carbon atom to which they are attached form a =CRR' group (e.g., =CH$_2$).

In additional embodiments, $R^5$ and $R^6$ are each independently hydrogen, halogen (e.g., Cl, Br, I), hydroxyl, alkyl (e.g., ethyl), alkenyl (e.g., —CH=CH$_2$), alkoxy (e.g., methoxy, OCHF$_2$), alkenyloxy (e.g., —OCH=CH$_2$), nitro, amino, alkylamino (e.g., —NHMe, —NHEt), dialkylamino (e.g., —NMe$_2$) or —C(O)OR$^8$ (e.g., —C(O)OEt).

In further embodiments, $R^5$ is hydrogen, halogen (e.g., Cl, Br), hydroxyl, alkoxy (e.g., methoxy, —OCHF$_2$), alkenyloxy (e.g., —OCH=CH$_2$) or alkylamino (e.g., —NHMe).

In further embodiments, $R^6$ is hydrogen, halogen (e.g., Cl, Br, I), alkyl (e.g., ethyl), alkenyl (e.g., —CH=CH$_2$), nitro, amino, alkylamino (e.g., —NHEt), dialkylamino (e.g., —NMe$_2$) or —C(O)OR$^8$ (e.g., —C(O)OEt).

In one embodiment, $R^5$ is hydroxyl, alkoxy (e.g., OCH$_3$, OCHF$_2$) or alkenyloxy (e.g., —OCH=CH$_2$) and $R^6$ is hydrogen, halogen (e.g., Cl, Br, I), alkenyl (e.g., —CH=CH$_2$), alkyl (e.g., ethyl), nitro, amino, alkylamino (e.g., —NHEt), dialkylamino (e.g., —NMe$_2$) or —C(O)OR$^8$ (e.g., —C(O)OEt).

In additional embodiments, $R^7$ is hydrogen, alkyl, —C(O)R$^9$ or —C(O)OR$^9$, in which R$^9$ is independently hydrogen or alkyl. For example, $R^7$ is hydrogen, alkyl (e.g., methyl), —C(O)-alkyl (e.g., —C(O)CF$_3$) or —C(O)O-alkyl (e.g., —C(O)OEt). In certain embodiments, $R^7$ is hydrogen, or —C(O)OR$^9$ (e.g., —C(O)OEt). In one embodiment, $R^7$ is hydrogen. In another embodiment, $R^7$ is alkyl (e.g., methyl).

In further embodiments, $R^8$ is alkyl (e.g., methyl, ethyl). In further embodiments, $R^9$ and $R^{10}$ are independently hydrogen or alkyl (e.g., methyl, ethyl).

In an additional embodiment, one of $X^1$ and $X^2$ is N and the other is CR$^{12}$ (e.g., $X^1$ is N and $X^2$ is CR$^{12}$). In certain embodiments, R$^{12}$ is hydrogen, halogen (e.g., Cl, Br), alkyl (e.g., methyl), hydroxyl or alkoxy (e.g., —OCH$_3$).

In another embodiment, when $R^1$, $R^{1a}$, $R^2$, $R^{2a}$, $R^3$, $R^{3a}$, $R^4$ and $R^{4a}$ are hydrogen, at least one of $R^5$ and $R^6$ is hydroxyl, alkoxy or alkenyloxy.

In one embodiment, $X^1$ is N, $X^2$ is CR$^{12}$ and $R^5$, $R^6$ and R$^{12}$ are other than H. For example, in certain embodiments, $X^1$ is N, $X^2$ is CR$^{12}$ where R$^{12}$ is halogen (e.g., Br, Cl), hydroxyl or alkoxy (e.g., —OCH$_3$), and $R^5$ and $R^6$ are independently halogen (e.g., Cl, Br), alkoxy (e.g., —OCH$_3$), amino, alkylamino (e.g., —NHEt), dialkylamino (e.g., —NMe₂) or —C(O)OR⁸ (e.g., —C(O)OEt).

In another embodiment, one of R¹, R¹ᵃ, R², R²ᵃ, R³, R³ᵃ, R⁴ and R⁴ᵃ is other than hydrogen (e.g., R¹ is alkyl (e.g., methyl) and R¹ᵃ, R², R²ᵃ, R³, R³ᵃ, R⁴ and R⁴ᵃ are hydrogen), X¹ is N, X² is CR¹² where R¹² is hydrogen or halogen (e.g., Cl), R⁵ is alkoxy (e.g., methoxy) and R⁶ is halogen (e.g., Br, Cl) or alkylamino (e.g., —NHEt).

In certain embodiments, R⁵ and R⁶ together with the carbon atoms to which they are attached form an optionally substituted 5 or 6-membered aromatic or non-aromatic heterocyclic ring that does not contain a sulfur atom. For example, R⁵ and R⁶ together with the carbon atoms to which they are attached form an optionally substituted 5 or 6-membered aromatic or non-aromatic heterocyclic ring other than thiene, dihydrothiene or thiazole. In further embodiments, R⁵ and R⁶ together with the carbon atoms to which they are attached form an optionally substituted 5 or 6-membered aromatic or non-aromatic heterocyclic ring containing one or more oxygen atoms.

In exemplary embodiments, R⁵ and R⁶ together with the carbon atoms to which they are attached form an optionally substituted aromatic or non-aromatic heterocyclic ring selected from pyran, pyrazine, pyrimidine, oxazine, pyridazine, furan, pyrrole, imidazole, dihydropyrrole and pyrazole. In one embodiment, R⁵ and R⁶ together with the carbon atoms to which they are attached form an optionally substituted 5-membered aromatic or non-aromatic heterocyclic ring containing an oxygen atom (e.g., furan, 3-methylfuran)

One of ordinary skill in the art will readily appreciate that compounds of formula I may exist in different tautomeric forms. As an example, when R⁵ is hydroxyl, the compound of formula I may exist as the two tautomeric forms shown below:

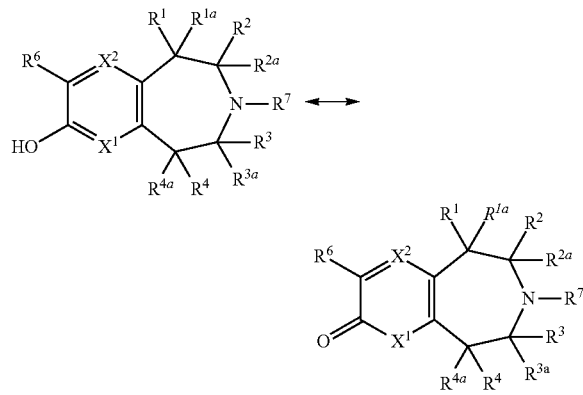

As a further example, when X² is CR¹¹ and R¹¹ is hydroxyl, the compound of formula I may exist as the two tautomeric forms shown below:

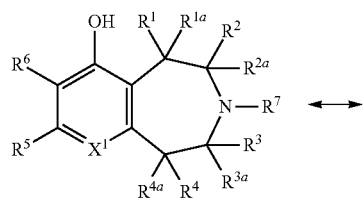

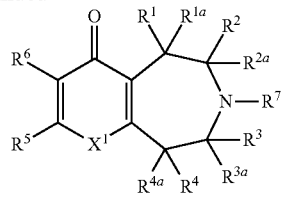

These tautomeric forms are used interchangebably herein, and all tautomeric forms are encompassed within the present invention.

In certain embodiments, the compound of formula I is selected from:
3-bromo-2-methoxy-5,8-dimethyl-6,7,8,9-tetrahydro-5H-pyrido[2,3-d]azepine,
2-methoxy-5-methylene-6,7,8,9-tetrahydro-5H-pyrido[2,3-d]azepine,
2-methoxy-5-methyl-6,7,8,9-tetrahydro-5H-pyrido[2,3-d]azepine,
5-methyl-6,7,8,9-tetrahydro-5H-pyrido[2,3-d]azepin-2-ol,
3-bromo-2-methoxy-5-methyl-6,7,8,9-tetrahydro-5H-pyrido[2,3-d]azepine,
3-chloro-2-methoxy-5-methyl-6,7,8,9-tetrahydro-5H-pyrido[2,3-d]azepine,
3-bromo-5-methyl-6,7,8,9-tetrahydro-5H-pyrido[2,3-d]azepin-2-ol,
3-iodo-5-methyl-6,7,8,9-tetrahydro-5H-pyrido[2,3-d]azepin-2-ol,
2-chloro-3-iodo-5-methyl-6,7,8,9-tetrahydro-5H-pyrido[2,3-d]azepine,
3-iodo-2-methoxy-5-methyl-6,7,8,9-tetrahydro-5H-pyrido[2,3-d]azepine,
3-iodo-1,5-dimethyl-1,5,6,7,8,9-hexahydro-2H-pyrido[2,3-d]azepin-2-one,
2-(allyloxy)-3-iodo-5-methyl-6,7,8,9-tetrahydro-5H-pyrido[2,3-d]azepine,
3,5-dimethyl-6,7,8,9-tetrahydro-5H-furo[3',2':5,6]pyrido[2,3-d]azepine,
2-chloro-5-methyl-6,7,8,9-tetrahydro-5H-pyrido[2,3-d]azepine,
3-bromo-2-chloro-5-methyl-6,7,8,9-tetrahydro-5H-pyrido[2,3-d]azepine,
2-methoxy-5-methyl-3-vinyl-6,7,8,9-tetrahydro-5H-pyrido[2,3-d]azepine,
3-ethyl-2-methoxy-5-methyl-6,7,8,9-tetrahydro-5H-pyrido[2,3-d]azepine,
2-(difluoromethoxy)-5-methyl-6,7,8,9-tetrahydro-5H-pyrido[2,3-d]azepine,
3-bromo-N,5-dimethyl-6,7,8,9-tetrahydro-5H-pyrido[2,3-d]azepin-2-amine,
2-methoxy-5-methyl-3-nitro-6,7,8,9-tetrahydro-5H-pyrido[2,3-d]azepine,
2-methoxy-5-methyl-6,7,8,9-tetrahydro-5H-pyrido[2,3-d]azepin-3-amine,
2-methoxy-N,N,5-trimethyl-6,7,8,9-tetrahydro-5H-pyrido[2,3-d]azepin-3-amine,
4-bromo-2-methoxy-5-methyl-6,7,8,9-tetrahydro-5H-pyrido[2,3-d]azepin-3-amine,
N-ethyl-2-methoxy-5-methyl-6,7,8,9-tetrahydro-5H-pyrido[2,3-d]azepin-3-amine,
4-chloro-N-ethyl-2-methoxy-5-methyl-6,7,8,9-tetrahydro-5H-pyrido[2,3-d]azepin-3-amine,
3,4-dibromo-2-methoxy-5-methyl-6,7,8,9-tetrahydro-5H-pyrido[2,3-d]azepine, 3-bromo-4-chloro-2-methoxy-5-methyl-6,7,8,9-tetrahydro-5H-pyrido[2,3-d]azepine,
3,4-dichloro-2-methoxy-5-methyl-6,7,8,9-tetrahydro-5H-pyrido[2,3-d]azepine,
5-methyl-6,7,8,9-tetrahydro-5H-pyrido[2,3-d]azepin-3-amine,
3-bromo-5-methyl-6,7,8,9-tetrahydro-5H-pyrido[2,3-d]azepine,
3-bromo-2-methoxy-6,7,8,9-tetrahydro-5H-pyrido[2,3-d]azepin-4-ol,
2,4-dimethoxy-6,7,8,9-tetrahydro-5H-pyrido[2,3-d]azepine,
2-methoxy-6,7,8,9-tetrahydro-5H-pyrido[2,3-d]azepin-4-ol,
2,4-dimethoxy-6,7,8,9-tetrahydro-5H-pyrido[2,3-d]azepine-3-carboxylic acid ethyl ester,
2-bromo-9-methyl-6,7,8,9-tetrahydro-5H-pyrido[2,3-d]azepine,
9-methyl-6,7,8,9-tetrahydro-5H-pyrido[2,3-d]azepine-2,4-diol, and
3,4-dibromo-2-methoxy-5,7-dimethyl-6,7,8,9-tetrahydro-5H-pyrido[2,3-d]azepine, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

In another embodiment, the compound of Formula I is selected from
  (5R)-3-bromo-2-methoxy-5-methyl-6,7,8,9-tetrahydro-5H-pyrido[2,3-d]azepine,
  (5S)-3-bromo-2-methoxy-5-methyl-6,7,8,9-tetrahydro-5H-pyrido[2,3-d]azepine,
  (5R)-4-chloro-N-ethyl-2-methoxy-5-methyl-6,7,8,9-tetrahydro-5H-pyrido[2,3-d]azepin-3-amine,
  (5S)-4-chloro-N-ethyl-2-methoxy-5-methyl-6,7,8,9-tetrahydro-5H-pyrido[2,3-d]azepin-3-amine,
  (5R)-3-bromo-4-chloro-2-methoxy-5-methyl-6,7,8,9-tetrahydro-5H-pyrido[2,3-d]azepine, and
  (5S)-3-bromo-4-chloro-2-methoxy-5-methyl-6,7,8,9-tetrahydro-5H-pyrido[2,3-d]azepine, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph.

In another embodiment, the compound of formula I is selected from:
  2-methoxy-8-methyl-5-methylene-7-(trifluoroacetyl)-6,7,8,9-tetrahydro-5H-pyrido[2,3-d]azepine,
  2-methoxy-5,8-dimethyl-7-(trifluoroacetyl)-6,7,8,9-tetrahydro-5H-pyrido[2,3-d]azepine,
  3-bromo-2-methoxy-5,8-dimethyl-7-(trifluoroacetyl)-6,7,8,9-tetrahydro-5H-pyrido[2,3-d]azepine,
  2-methoxy-5-methylene-7-(trifluoroacetyl)-6,7,8,9-tetrahydro-5H-pyrido[2,3-d]azepine,
  2-methoxy-5-methyl-7-(trifluoroacetyl)-6,7,8,9-tetrahydro-5H-pyrido[2,3-d]azepine,
  5-methyl-7-(trifluoroacetyl)-6,7,8,9-tetrahydro-5H-pyrido[2,3-d]azepin-2-ol,
  3-bromo-2-methoxy-5-methyl-7-(trifluoroacetyl)-6,7,8,9-tetrahydro-5H-pyrido[2,3-d]azepine,
  3-chloro-2-methoxy-5-methyl-7-(trifluoroacetyl)-6,7,8,9-tetrahydro-5H-pyrido[2,3-d]azepine,
  3-bromo-5-methyl-7-(trifluoroacetyl)-6,7,8,9-tetrahydro-5H-pyrido[2,3-d]azepin-2-ol,
  3-iodo-5-methyl-7-(trifluoroacetyl)-6,7,8,9-tetrahydro-5H-pyrido[2,3-d]azepin-2-ol,
  2-chloro-3-iodo-5-methyl-7-(trifluoroacetyl)-6,7,8,9-tetrahydro-5H-pyrido[2,3-d]azepine,
  3-iodo-2-methoxy-5-methyl-7-(trifluoroacetyl)-6,7,8,9-tetrahydro-5H-pyrido[2,3-d]azepine,
  3-iodo-1,5-dimethyl-7-(trifluoroacetyl)-1,5,6,7,8,9-hexahydro-2H-pyrido[2,3-d]azepin-2-one,
  2-(allyloxy)-3-iodo-5-methyl-7-(trifluoroacetyl)-6,7,8,9-tetrahydro-5H-pyrido[2,3-d]azepine,
  3,5-dimethyl-7-(trifluoroacetyl)-6,7,8,9-tetrahydro-5H-furo[3',2':5,6]pyrido[2,3-d]azepine,
  2-chloro-5-methyl-7-(trifluoroacetyl)-6,7,8,9-tetrahydro-5H-pyrido[2,3-d]azepine,
  3-bromo-2-chloro-5-methyl-7-(trifluoroacetyl)-6,7,8,9-tetrahydro-5H-pyrido[2,3-d]azepine,
  2-methoxy-5-methyl-7-(trifluoroacetyl)-3-vinyl-6,7,8,9-tetrahydro-5H-pyrido[2,3-d]azepine,
  3-ethyl-2-methoxy-5-methyl-7-(trifluoroacetyl)-6,7,8,9-tetrahydro-5H-pyrido[2,3-d]azepine,
  2-(difluoromethoxy)-5-methyl-7-(trifluoroacetyl)-6,7,8,9-tetrahydro-5H-pyrido[2,3-d]azepine,
  3-bromo-5-methyl-7-(trifluoroacetyl)-6,7,8,9-tetrahydro-5H-pyrido[2,3-d]azepin-2-yl trifluoromethanesulfonate,
  3-bromo-N,5-dimethyl-7-(trifluoroacetyl)-6,7,8,9-tetrahydro-5H-pyrido[2,3-d]azepin-2-amine,
  2-methoxy-5-methyl-3-nitro-7-(trifluoroacetyl)-6,7,8,9-tetrahydro-5H-pyrido[2,3-d]azepine,
  2-methoxy-5-methyl-7-(trifluoroacetyl)-6,7,8,9-tetrahydro-5H-pyrido[2,3-d]azepin-3-amine,
  2-methoxy-N,N,5-trimethyl-7-(trifluoroacetyl)-6,7,8,9-tetrahydro-5H-pyrido[2,3-d]azepin-3-amine,
  4-bromo-2-methoxy-5-methyl-7-(trifluoroacetyl)-6,7,8,9-tetrahydro-5H-pyrido[2,3-d]azepin-3-amine,
  N-ethyl-2-methoxy-5-methyl-7-(trifluoroacetyl)-6,7,8,9-tetrahydro-5H-pyrido[2,3-d]azepin-3-amine,
  4-chloro-N-ethyl-2-methoxy-5-methyl-7-(trifluoroacetyl)-6,7,8,9-tetrahydro-5H-pyrido[2,3-d]azepin-3-amine,
  3,4-dibromo-2-methoxy-5-methyl-7-(trifluoroacetyl)-6,7,8,9-tetrahydro-5H-pyrido[2,3-d]azepine,
  4-chloro-2-methoxy-5-methyl-7-(trifluoroacetyl)-6,7,8,9-tetrahydro-5H-pyrido[2,3-d]azepin-3-amine,
  3-bromo-4-chloro-2-methoxy-5-methyl-7-(trifluoroacetyl)-6,7,8,9-tetrahydro-5H-pyrido[2,3-d]azepine,
  3,4-dichloro-2-methoxy-5-methyl-7-(trifluoroacetyl)-6,7,8,9-tetrahydro-5H-pyrido[2,3-d]azepine,
  5-methyl-3-nitro-7-(trifluoroacetyl)-6,7,8,9-tetrahydro-5H-pyrido[2,3-d]azepin-2-ol,
  2-bromo-5-methyl-3-nitro-7-(trifluoroacetyl)-6,7,8,9-tetrahydro-5H-pyrido[2,3-d]azepine,
  5-methyl-7-(trifluoroacetyl)-6,7,8,9-tetrahydro-5H-pyrido[2,3-d]azepin-3-amine,
  3-bromo-5-methyl-7-(trifluoroacetyl)-6,7,8,9-tetrahydro-5H-pyrido[2,3-d]azepine,
  7-tert-butyl 3-ethyl 4-hydroxy-2-oxo-1,2,5,6,8,9-hexahydro-7H-pyrido[2,3-d]azepine-3,7-dicarboxylate, tert-butyl 4-hydroxy-2-oxo-1,2,5,6,8,9-hexahydro-7H-pyrido[2,3-d]azepine-7-carboxylate, tert-butyl 3-bromo-4-hydroxy-2-oxo-1,2,5,6,8,9-hexahydro-7H-pyrido[2,3-d]azepine-7-carboxylate, tert-butyl 3-bromo-4-hydroxy-2-methoxy-5,6,8,9-tetrahydro-7H-pyrido[2,3-d]azepine-7-carboxylate, tert-butyl 2,4-dimethoxy-5,6,8,9-tetrahydro-7H-pyrido[2,3-d]azepine-7-carboxylate, tert-butyl 4-hydroxy-2-methoxy-5,6,8,9-tetrahydro-7H-pyrido[2,3-d]azepine-7-carboxylate, 7-tert-butyl 3-ethyl 2,4-dimethoxy-5,6,8,9-tetrahydro-7H-pyrido[2,3-d]azepine-3,7-dicarboxylate, 7-tert-butyl 3-ethyl 4-hydroxy-9-methyl-2-oxo-1,2,5,6,8,9-hexahydro-7H-pyrido[2,3-d]azepine-3,7-dicarboxylate, tert-butyl 4-hydroxy-9-methyl-2-oxo-1,2,5,6,8,9-hexahydro-7H-pyrido[2,3-d]azepine-7-carboxylate, 4-hydroxy-9-methyl-7-(trifluoroacetyl)-1,5,6,7,8,9-hexahydro-2H-pyrido[2,3-d]azepin-2-one, 4-bromo-9-methyl-7-(trifluoroacetyl)-1,5,6,7,8,9-hexahydro-2H-pyrido[2,3-d]azepin-2-one, 9-methyl-7-(trifluoroacetyl)-1,5,6,7,8,9-hexahydro-2H-pyrido[2,3-d]azepin-2-one, and 2-bromo-9-methyl-7-(trifluoroacetyl)-6,7,8,9-tetrahydro-5H-pyrido[2,3-d]azepine, wherein free base forms listed above can also be in the form of a pharmaceutically acceptable salt wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof ) can also be in the form of a polymorph, and wherein if the compound exhibits chirality it can be in the form of a mixture of enantiomers such as a racemate or a mixture of diastereomers, or can be in the form of a single enantiomer or a single diastereomer.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one ore more halogens, such as, but not limited to, —$CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —$NH_2$.

The term "alkylamino" means —NH(alkyl), wherein alkyl is as described above.

The term "dialkylamino" means —$N(alkyl)_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —$N(aryl)_2$, wherein aryl is as described above.

The term "amido" means —$CONH_2$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro

[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previsouly described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl—C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "alkenyloxy" means alkenyl-O— groups in which the alkenyl portion is in accordance with the previous discussion. Suitable alkoxy groups include, but are not limited to, —OCH$_2$CH=CH$_2$.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of formula I can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formula I can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formula I can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formula I can exist in different solvate forms. Solvates of the compounds of the invention may also form when solvent molecules are incorporated into the crystalline lattice structure of the compound molecule during the crystallization process.

The present invention also includes prodrugs of compounds of formula I. The term prodrug is intended to represent covalently bonded carriers, which are capable of releasing the active ingredient of formula I when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of formula I include compounds wherein a hydroxy, amino, carboxylic or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of formula I), amides (e.g., trifluoroacetylamino, acetylamino, and the like), and the like. Prodrugs of compounds of formula I are also within the scope of this invention.

Processes for preparing the compounds of the present invention are also provided. For example, the compounds of formula I may be prepared using the following general reaction scheme:

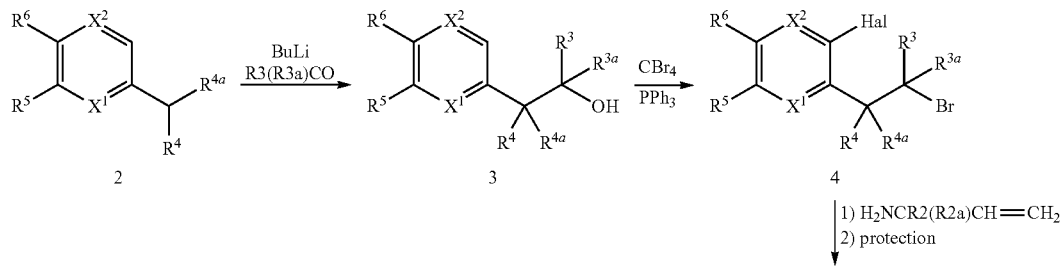

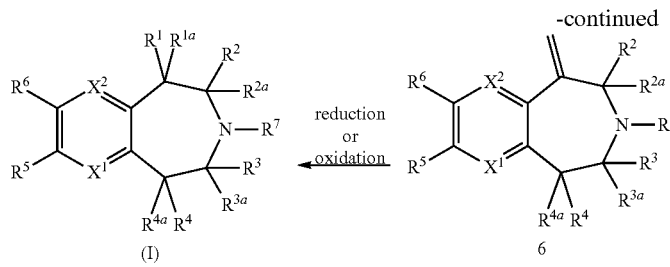

The methyl group of a suitably substituted pyridine 2 is alkylated with an appropriate aldehyde (R3$^a$=H) to generate a 2-hydroxyalkyl group 3. The 3-position of the pyridine ring is halogenated and the recently installed 2-hydroxyalkyl group is converted to the corresponding 2-bromoalkyl group to afford 4. The aliphatic bromine in 4 is displaced with an appropriately substituted allylamine followed by protection of the resulting amine with an amino protecting group. Cyclization to afford 6 may be achieved by a Heck reaction using a variety of palladium catalysts in combination with a suitable organic or inorganic base. The alkene formed in the Heck reaction may then be converted to a compound of formula I.

Methods for the preparation of compounds of formula (I) in which $R^7$ is —S(O)$_2$R$^{11}$ or —S(O)R$^{11}$ would be known to one of ordinary skill in the art. For example, sulfonamides and sulfinamides may be prepared by reacting sulfonyl halides and sulfinyl halides with amines in the presence of a common base. In addition, it would readily be apparent to one of ordinary skill in the art that tertiary sulfonamides and sulfinamides may be obtained by alkylation of secondary sulfonamides and sulfinamides.

The compounds of the invention can be administered alone or as an active ingredient of a formulation. Thus, the present invention also includes pharmaceutical compositions of compounds of formula I, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intraveneously, intramuscularly, intrastemally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds according to the invention can be administered by inhalation in the form of a powder (e.g., micronized) or in the form of atomized solutions or suspensions. The aerosol formulation can be placed into a pressurized acceptable propellant.

The compounds of formula I may be useful as ligands for 5-HT receptors, for example, 5HT$_2$c. Therefore, the compounds of formula I may be useful in the treatment of conditions mediated by 5-HT receptors, for example, 5HT$_2$c. In certain embodiments, the compounds of the present invention may be useful in the treatment of conditions that respond to a 5-HT receptor agonist, inverse agonist or antagonist.

The present invention further provides methods of modulating a 5HT (e.g., 5HT$_2$c) receptor comprising contacting said receptor with a pharmaceutically effective amount of a compound or composition of the invention. In one embodiment, said compound is an agonist of said receptor.

The present invention further provides methods of prophylaxis or treatment of disorders of the central nervous system; damage to the central nervous system; cardiovascular disorders; gastrointestinal disorders; diabetes insipidus, and sleep apnea comprising administering to a patient in need of such prophylaxis or treatment an effective amount of a compound of the invention.

In some embodiments, the disorders of the central nervous system include, but are not limited to, depression, atypical depression, bipolar disorders, anxiety disorders, obsessive-compulsive disorders, social phobias or panic states, sleep disorders, sexual dysfunction, psychoses, schizophrenia, migrane and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related mental disorders, chronic fatigue syndrome, drug and alcohol addiction, obesity, bulimia, anorexia nervosa and premenstrual tension. In some embodiments, the disorder of the central nervous system is obesity.

In some embodiments, the damage to the central nervous system is by trauma, stroke, neurodegenerative diseases or toxic or infective CNS diseases, including encephalitis and meningitis.

In some embodiments, the cardiovascular disorder is thrombosis. In further embodiments, the gastrointestinal disorder is dysfunction of gastrointestinal motility.

The present invention further provides methods of decreasing food intake of a patient comprising administering to said patient a pharmaceutically effective amount of a compound or composition of the invention.

The present invention further provides methods of inducing satiety in a patient comprising administering to said patient a pharmaceutically effective amount of a compound or composition of the invention.

The present invention further provides methods of controlling weight gain of a patient comprising administering to said patient a pharmaceutically effective amount of a compound or composition of the invention.

The present invention further provides methods of treating obesity comprising administering to a patient in need of such treatment a pharmaceutically effective amount of a compound or composition of the invention.

In some embodiments, some of the foregoing methods of the invention further comprising the step of identifying a subject, said subject being in need of decreasing food intake, controlling weight gain, or treating obesity, wherein said identifying step is performed prior to administering to said subject said pharmaceutically effective amount of said compound or composition of the invention.

One aspect of the present invention pertains to a compound of formula I for use in a method of treatment of the human or animal body by therapy.

One aspect of the present invention pertains to a compound of formula I for use in a method of prophylaxis or treatment of disorders of the central nervous system; damage to the central nervous system; cardiovascular disorders; gastrointestinal disorders; diabetes insipidus, and sleep apnea. In some embodiments the disorders of the central nervous system are depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension. In some embodiments the disorder is obesity.

One aspect of the present invention pertains to a compound of formula I for the manufacture of a medicament for use in the propylaxis or treatment of disorders of the central nervous system; damage to the central nervous system; cardiovascular disorders; gastrointestinal disorders; diabetes insipidus, and sleep apnea. In some embodiments the disorders of the central nervous system are depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension. In some embodiments the disorder is obesity.

In some embodiments, the invention provides methods for alleviation of a symptom of any of the diseases, conditions or disorders mentioned herein.

The compounds of formula I can be used in the prophylaxis or treatment of central nervous disorders such as, but are not limited to, depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula I in the manufacture of a medicament for the prophylaxis or treatment of the disorders disclosed herein. In one embodiment, there is provided a use of a compound of formula I in the manufacture of a medicament for the prophylaxis or treatment of obesity.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of formula I that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of formula I may be used in combination with other drugs or therapies that are used in the treatment/prevention/suppression or amelioration of the diseases or conditions for which compounds of formula I are useful.

Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I may be employed. Accordingly, the pharmaceutical compositions of the present invention include those that also contain one or more other active ingredients, in addition to a compound of formula I.

EXAMPLES

The present invention will now be further described by way of the following non-limiting examples. In applying the disclosure of these examples, it should be kept clearly in mind that other and different embodiments of the methods and schemes disclosed herein will no doubt suggest themselves to those of ordinary skill in the relevant art.

In the foregoing and in the following examples, all temperatures are set forth uncorrected in degrees Celsius; and, unless otherwise indicated, all parts and percentages are by weight.

The following abbreviation are used herein: Ac (acetyl), DCM (dichloromethane), DCC (NN'-dicyclohexylcarbodiimide), DEA (diethylamine), DMA (N,N'-dimethylacetamide), Et (ethyl), EtOAc (ethyl acetate), EtOH (ethanol), HMPA (hexamethylphosphoramide), Me (methyl, $CH_3$), MeOH (methanol), NBS (N-bromo succinimide), TFA (trifluoroacetic acid), TFAA (trifluoroacetic acid anhydride), THF (tetrahydrofuran), Bu (butyl), MsCl (methanesulfonyl chloride), $Et_3N$ (triethylamine), HPLC (high performance liquid chromatography), NMR (nuclear magnetic resonance spectroscopy), DMF (N,N'-dimethylformamide), DCE (1,2-dichloroethane), MS (mass spectroscopy), Pr (propyl), ESI (electro spray ionisation), Tf (trifluoromethanesulfonyl), ppm (pars per million).

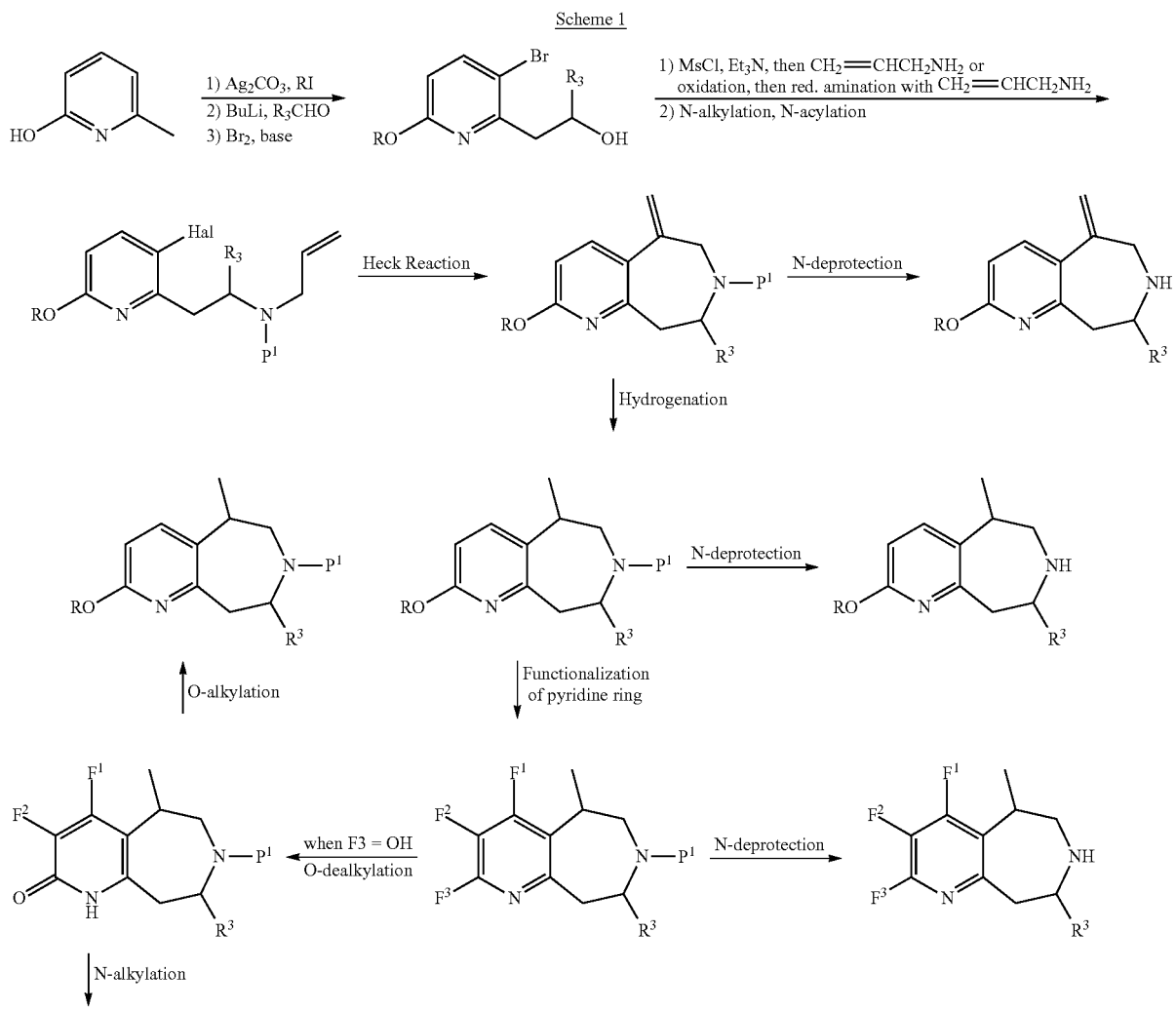

Scheme 1

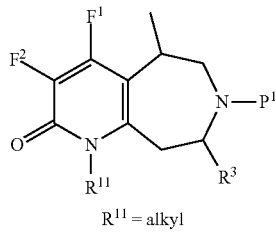

R¹¹ = alkyl

F1 = H, halogen
F2 = H, halogen, NO2, amino, alkylamino, dialkylamino
F3 = H, halogen, OH, amino, alkylamino, dialkylamino
R = alkyl, R3 = alkyl
P1 = protecting group
(alkyl, aryl, COX, SO2X, etc. X = leaving group)

1) 3-Bromo-2-methoxy-5,8-dimethyl-6,7,8,9-tetrahydro-5H-pyrido[2,3-d]azepine

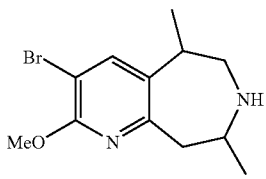

A mixture of 2-hydroxy-6-methylpyridine (164 g, 1.47 mol), iodomethane (1.35 kg, 9.53 mol), Ag$_2$CO$_3$ (526 g, 1.91 mol) in THF (10 ml) was strirred overnight at ambient temperature while protecting from light. The mixture was filtered through Celite and the filter cake was washed with THF. The filtrate was concentrated in vacuo until all methyl iodide was removed by HPLC analysis to yield 145.6 g (80%) of 2-methoxy-6-methylpyridine. BuLi (2.5 M, 49.0 ml, 122 mmol) was added to a solution of 2-methoxy-6-methylpyridine in THF (300 ml) at −78° C. over a period of 30 min. After warming the mixture to 0° C. over a period of 1 h, the reaction was re-cooled to −78° C. and acetaldehyde (22.3 ml, 407 mmol) was slowly added. The mixture was stirred for 1 h at −78° C. and allowed to warm to ambient temperature. Addition of sat. aq. NH$_4$Cl and extraction with EtOAc was followed by a wash of the organic layer with sat. aq. NaHCO$_3$ and brine. Concentration of the organic layer in vacuo and chromatographic purification of the resulting residue gave 8.96 g (66%) of 1-(6-methoxypyridin-2-yl)propan-2-ol. $^1$H-NMR (CDCl$_3$) δ 7.51 (dd, 1H), 6.71 (d, 1H), 6.63 (d, 1H), 5.18 (br s, 1H), 4.21 (qdd, 1H), 3.91 (s, 3H), 2.84 (dd, 1H), 2.77 (dd, 1H), 1.28 (d, 3H) ppm. Br$_2$ (8.41 g, 52.6 mmol) was added dropwise to a mixture of 1-(6-methoxypyridin-2-yl)propan-2-ol (5.00 g, 32.6 mmol), Na$_2$HPO$_4$ buffer (0.15 M, 1.20 l) and MeOH (15 ml). After stirring for 16 h at ambient temperature, the reaction mixture was parted between EtOAc and NaHCO$_3$. The organic phase was washed with brine, dried over Na$_2$SO$_4$ and concentrated in vacuo. Chromatographic purification rendered 8.29 g (63%) of 1-(3-bromo-6-methoxypyridin-2-yl)propan-2-ol. $^1$H-NMR (CDCl$_3$) δ 7.70 (dd, 1H), 6.56 (d, 1H), 4.65 (br s, 1H), 4.36 (qdd, 1H), 3.91 (s, 3H), 3.10 (dd, 1H), 2.83 (dd, 1H), 1.34 (d, 3H) ppm. To a mixtrue of pyridine (2.17 ml, 26.8 mmol) and TFA (1.08 ml) in toluene (40 ml) was added a solution of 1-(3-bromo-6-methoxypyridin-2-yl)propan-2-ol (6.60 g, 26.8 mmol) in DMF (27 ml). The mixture was stirred for 5 h and, after addition of DCC (5.53 g, 26.8 mmol), an extra 2 h at ambient temperature. The mixture was diluted with Et$_2$O (400 ml) and a solution of oxalic acid (18.0 g, 112 mmol) in MeOH (67 ml) was added which resulted in formation of CO$_2$. After filtration of the precipitate, the filter cake was washed with Et$_2$O and the filtrate was extracted with sat. aq. NaHCO$_3$, washed with brine and dried over Na$_2$SO$_4$. Concentration of the organic layer in vacuo and chromatographic purification of the resulting residue gave 6.70 g (99%) of 1-(3-bromo-6-methoxypyridin-2-yl)acetone. $^1$H-NMR (CDCl$_3$) δ 7.66 (dd, 1H), 6.55 (d, 1H), 3.98 (s, 2H), 3.86 (s, 3H), 2.23 (s, 3H) ppm. A mixture of 1-(3-bromo-6-methoxypyridin-2-yl)acetone (267 mg, 1.09 mmol), allylamine (90.0 μl, 1.20 mmol), AcOH (314 μl), and DCE (10 ml) was stirred for 5 min at room temperature, then NaBH(OAc)$_3$ (700 mg, 3.27 mmol) was added and it was stirred for another 3 h at ambient temperature. The mixture was diluted with DCM, washed with sat. aq. NaHCO$_3$, dried over Na$_2$SO$_4$, and concentrated in vacuo. The crude residue was dissolved in DCM (3 ml) and Et$_3$N (310 ml, 2.20 μmol) and TFAA (154 ml, 1.1 μmol) were added. After stirring for 5 min, the mixture was diluted with DCM, washed with sat. aq. NaHCO$_3$, dried over Na$_2$SO$_4$, concentrated in vacuo and chromatographically purified to give 282 mg (68%) of N-allyl-N-[2-(3-bromo-6-methoxypyridin-2-yl)-1-methylethyl]-2,2,2-trifluoroacetamide. $^1$H-NMR of rotamers (CDCl$_3$) δ 7.65 (d, 0.5H), 7.63 (d, 0.5H), 6.53 (d, 0.5H), 6.51 (d, 0.5H), 5.94 (dddd, 0.5H), 5.66 (dddd, 0.5H), 5.32-5.16 (m, 2H), 4.78 (qd, 0.5H), 4.51 (qd, 0.5H), 4.20 (dd, 0.5H), 4.04 (dd, 0.5H), 3.95 (dd, 0.5H), 3.88 (s, 1.5H), 3.99 (s, 1.5H), 3.79 (dd, 0.5H), 3.39 (dd, 0.5H), 3.25 (dd, 0.5H), 3.19 (dd, 0.5H), 3.02 (dd, 0.5H), 1.43 (d, 1.5H), 1.31 (d, 1.5H) ppm. A mixture of N-allyl-N-[2-(3-bromo-6-methoxypyridin-2-yl)-1-methylethyl]-2,2,2-trifluoroacetamide (265 mg, 696 μmol), NaOAc (171 mg, 2.09 mmol), (Ph$_3$P)$_2$PdCl$_2$ (244 mg, 348 μmol), and DMA (5 ml) was heated at 130° C. for 1 h. The reaction mixture was diluted with EtOAc, filtered through Celite and concentrated in vacuo. Chromatographic purification rendered 169 mg (81%) of 2-methoxy-8-methyl-5-methylene-7-(trifluoroacetyl)-6,7,8,9-tetrahydro-5H-pyrido[2,3-d]azepine. Hydrogenation of the resulting olefin (142 mg, 473 μmol) was carried out with 5% Pd/C (100 mg) in MeOH (3 ml) under H$_2$ (1 atm). Filtration and concentration of the reaction mixture yielded 142 mg (99%) of the desired alkane. The resulting 2-methoxy-5,8-dimethyl-7-(trifluoroacetyl)-6,7,8,9-tetrahydro-5H-pyrido[2,3-d]azepine was brominated in Na$_2$HPO$_4$ buffer (0.15 M, 17 ml) and MeOH (6 ml) by slow addition of Br$_2$ (144 μl, 2.81 mmol). After stirring for 16 h at ambient temperature, the reaction mixture was parted between EtOAc and NaHCO$_3$. The organic phase was washed with brine, dried over Na$_2$SO$_4$ and concentrated in vacuo. Chromatographic purification rendered 120 mg (81%) of 3-bromo-2-methoxy-5,8-dimethyl-7-(trifluoroacetyl)-6,7,8, 9-tetrahydro-5H-pyrido[2,3-d]azepine. A mixture of 3-bromo-2-methoxy-5,8-dimethyl-7-(trifluoroacetyl)-6,7,8, 9-tetrahydro-5H-pyrido[2,3-d]azepine (109 mg, 286 μmol), K$_2$CO$_3$ (200 mg, 1.45 mmol), and MeOH (10 ml) was refluxed for 8 h. Evaporation of the solvent was followed by addition of aq. sat. NaHCO$_3$ and subsequent extraction with EtOAc. The organic layer was dried, concentrated in vacuo and purified by column chromatography to furnish 64 mg (79%) of 3-bromo-2-methoxy-5,8-dimethyl-6,7,8,9-tetrahydro-5H-pyrido[2,3-d]azepine. $^1$H-NMR (CDCl$_3$) δ 7.58 (s, 1H), 4.00 (s, 3H), 3.13-2.88 (m, 5H), 2.61 (dd, 1H), 1.31 (d, 3H), 1.27 (d, 3H) ppm.

2) 2-Methoxy-5-methylene-6,7,8,9-tetrahydro-5H-pyrido[2,3-d]azepine

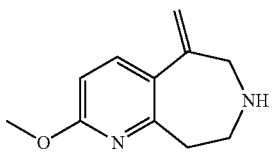

2-Methoxy-6-methylpyridine was diluted with THF to a total volume of 20 ml. It was cooled to −78° C. and treated with nBuLi (2.5 M in hexane, 4.8 ml, 11.9 mmol). After 15 min at −78° C., HMPA (2.1 ml, 11.92 mmol) was added and the mixture was allowed to warm to 0° C. Paraformaldehyde (1.38 g, 45.85 mmol) was added and the mixture was allowed to gradually warm to ambient temperature. The reaction was quenched with NH$_4$Cl and extracted with EtOAc. The organic layer was dried, concentrated in vacuo and purified by column chromatography to render 0.45 g (32%) of 2-(6-methoxypyridin-2-yl)ethanol. $^1$H-NMR (CDCl$_3$) δ 7.49 (dd, 1H), 6.72 (d, 1H), 6.60 (d, 1H), 4.46 (br s, 1H), 3.99 (t, 2H) 3.88 (s, 3H), 2.92 (t, 2H) ppm. Br$_2$ (1.67 ml, 32.6 mmol) was added dropwise to a mixture of 2-(6-methoxypyridin-2-yl)ethanol (5.00 g, 32.6 mmol), Na$_2$HPO$_4$ buffer (1.0 l) and MeOH (110 ml). After stirring for 12 h at ambient temperature, the reaction mixture was parted between EtOAc and NaHCO$_3$. The organic phase was washed with brine, dried over Na$_2$SO$_4$ and concentrated in vacuo. Chromatographic purification rendered 7.00 g (93%) of 2-(3-bromo-6-methoxypyridin-2-yl) ethanol. $^1$H-NMR (CDCl$_3$) δ 7.69 (d, 1H), 6.56 (d, 1H), 4.06 (t, 2H), 3.91 (s, 3H), 3.08 (t, 2H) ppm. To a solution of 2-(3-bromo-6-methoxypyridin-2-yl)ethanol (23.4 g, 0.10 mol) in DCM (468 ml) were added Et$_3$N (13.6 g, 0.131 mol) and MsCl (12.1 g, 0.106 mol) at 0-5° C. After 30 min, the reaction mixture was quenched with sat. aq. NaHCO$_3$ and extracted with DCM. The organic phase was successively washed with water and brine, and then dried over Na$_2$SO$_4$ and concentrated in vacuo to give 32.5 g (99%) of 3-bromo-2-(2-methanesulfonyloxyethyl)-6-methoxypyridine. H-NMR (CDCl$_3$) δ 7.68 (d, 1H), 6.56 (d, 1H), 4.74 (t, 2H), 3.92 (s, 3H), 3.32 (t, 2H), 3.00 (s, 3H) ppm. A mixture of 3-bromo-2-(2-methanesulfonyloxyethyl)-6-methoxypyridine (31.3 g, 0.10 mol), allylamine (90.5 ml, 1.21 mol) in acetonitrile (156 ml) was stirred at room temperature for 2 d. The reaction mixture was concentrated in vacuo, diluted with ethyl acetate, washed with sat. aq. NaHCO$_3$ and water, and then dried over Na$_2$SO$_4$. After concentration in vacuo, the crude product was dissolved in DCM (273 ml) and reacted with Et$_3$N (25.9 ml, 0.186 mol) and TFAA (15.4 ml, 0.11 mol) for 10 min at 5-10° C. The reaction mixture was parted between EtOAc and NaHCO$_3$ and the organic phase was washed with brine, dried over Na$_2$SO$_4$ and concentrated in vacuo. Chromatographic purification rendered 25.4 g (69%) of N-allyl-N-[2-(3-bromo-6-methoxypyridin-2-yl)ethyl]-2,2,2-trifluoroacetamide. $^1$H-NMR (CDCl$_3$) δ 7.64 (d), 7.62 (d), 6.52 (d), 6.51 (d), 5.82 (dddd), 5.72 (dddd), 5.28-5.18 (m), 4.11 (m), 3.91 (d), 3.91 (s), 3.81 (m), 3.16 (t) ppm. A mixture of N-allyl-N-[2-(3-bromo-6-methoxypyridin-2-yl)ethyl]-2,2,2-trifluoroacetamide (5.20 g, 14.2 mmol), (PPh$_3$)$_2$PdCl$_2$ (4.98 g, 7.08 mmol), NaOAc (3.49 g, 42.5 mmol) and DMA (100 ml) was stirred for 24 h at 130° C. Evaporation of solvent and chromatographic purification of the residue yielded 2.50 g (62%) of 2-methoxy-5-methylene-7-(trifluoroacetyl)-6,7,8,9-tetrahydro-5H-pyrido[2,3-d]azepine. $^1$H-NMR (CDCl$_3$) δ 7.51 (d, 1H), 6.61 (d, 1H), 5.39 (d, 1H), 5.30 (d, 1H), 4.43 (d, 2H), 3.94-3.87 (m, 5H), 3.20 (m, 2H) ppm. A mixture of 2-methoxy-5-methylene-7-(trifluoroacetyl)-6,7,8,9-tetrahydro-5H-pyrido[2,3-d]azepine (100 mg, 349 μmol) and K$_2$CO$_3$ (110 mg) in MeOH (6 ml) was heated for 1 h at 60° C. The reaction mixture was concentrated in vacuo and chromatographic purification rendered 39 mg (59%) of 2-methoxy-5-methylene-6,7,8,9-tetrahydro-5H-pyrido[2,3-d]azepine. $^1$H-NMR (CDCl$_3$) δ 7.47 (d, 1H), 6.58 (d, 1H), 5.28 (d, 1H), 5.21 (d, 1H), 3.93 (s, 3H), 3.64 (d, 2H), 3.19 (m, 2H), 3.10 (m, 2H) ppm.

3) 2-Methoxy-5-methyl-6,7,8,9-tetrahydro-5H-pyrido[2,3-d]azepine

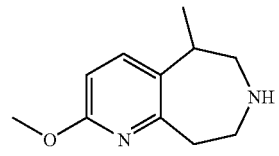

A mixture of 2-methoxy-5-methylene-7-(trifluoroacetyl)-6,7,8,9-tetrahydro-5H-pyrido[2,3-d]azepine (495 mg, 1.73 mmol), 10% Pd/C (60 mg) and MeOH (40 ml) was stirred under a H$_2$ atmosphere (1 atm) for 2 h at ambient temperature. Filtration and concentration of the filtrate in vacuo gave 490 mg (98%) of 2-methoxy-5-methyl-7-(trifluoroacetyl)-6,7,8,9-tetrahydro-5H-pyrido[2,3-d]azepine. $^1$H-NMR (DMSO-d$_6$) δ 7.52 (d, 1H), 6.65 (m, 1H), 3.94-3.73 (m, 5H), 3.65-3.44 (m, 2H), 3.24-3.05 (m, 3H), 1.20 (m, 3H) ppm. A mixture of 2-methoxy-5-methyl-7-(trifluoroacetyl)-6,7,8,9-tetrahydro-5H-pyrido[2,3-d]azepine (97.0 mg, 346 μmol) and K$_2$CO$_3$ (100 mg) in MeOH (10 ml) was heated at reflux for 2 h. The reaction mixture was parted between EtOAc and NaHCO$_3$.The organic phase was washed with brine, dried over Na$_2$SO$_4$ and concentrated in vacuo. Chromatographic purification rendered 63 mg (95%) of 2-methoxy-5-methyl-6,7,8,9-tetrahydro-5H-pyrido[2,3-d]azepine. $^1$H-NMR (CDCl$_3$) δ 7.35 (d, 1H), 6.51 (d, 1H), 3.90 (s, 3H), 3.10 (m, 2H), 3.04-2.93 (m, 4H), 2.75 (dd, 1H), 1.30 (d, 3H) ppm.

4) 5-Methyl-6,7,8,9-tetrahydro-5H-pyrido[2,3-d]azepin-2-ol

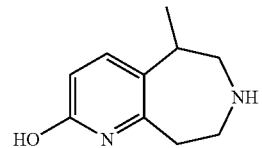

2-Methoxy-5-methyl-7-(trifluoroacetyl)-6,7,8,9-tetrahydro-5H-pyrido[2,3-d]azepine (1.99 g, 6.90 mmol) in 48% aq. HBr (15 ml) was heated at reflux for 18 h. Evaporation of aq. HBr rendered 1.78 g (99%) of hydrobromide salt of 5-methyl-6,7,8,9-tetrahydro-5H-pyrido[2,3-d]azepin-2-ol. $^1$H-NMR (D$_2$O) δ 7.78 (d, 1H), 6.66 (d, 1H), 3.55-3.10 (m, 7H), 1.36 (d, 3H) ppm.

5) 3-Bromo-2-methoxy-5-methyl-6,7,8,9-tetrahydro-5H-pyrido[2,3-d]azepine

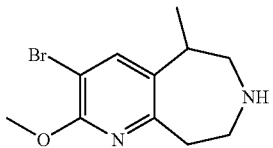

Br$_2$ (2.00 ml, 39.2 mmol) was added to a mixture of 2-methoxy-5-methyl-7-(trifluoroacetyl)-6,7,8,9-tetrahydro-5H-pyrido[2,3-d]azepine (113 mg, 392 μmol), Na$_2$HPO$_4$ buffer (40 ml) and MeOH (5 ml). After stirring for 1 h at ambient temperature, the reaction mixture was parted between EtOAc and NaHCO$_3$. The organic phase was washed with brine, dried over Na$_2$SO$_4$ and concentrated in vacuo. Chromatographic purification rendered 152 mg (99%) of 3-bromo-2-methoxy-5-methyl-7-(trifluoroacetyl)-6,7,8,9-tetrahydro-5H-pyrido[2,3-d]azepine. $^1$H-NMR (CDCl$_3$) δ 7.61 (s, 1H), 4.18-3.82 (m, 5H), 3.63 (m, 1H), 3.56-3.36 (m, 1H), 3.24 (m, 1H), 3.10 (m, 2H), 1.33 (m, 3H) ppm. A mixture of 3-bromo-2-methoxy-5-methyl-7-(trifluoroacetyl)-6,7,8,9-tetrahydro-5H-pyrido[2,3-d]azepine (52.0 mg, 142 μmol) and K$_2$CO$_3$ (100 mg) in MeOH (20 ml) was heated at reflux for 1.5 h. The reaction mixture was parted between EtOAc and NaHCO$_3$. The organic phase was washed with brine, dried over Na$_2$SO$_4$ and concentrated in vacuo. Chromatographic purification rendered 37.5 mg (97%) of 3-bromo-2-methoxy-5-methyl-6,7,8,9-tetrahydro-5H-pyrido[2,3-d]azepine. $^1$H-NMR (CDCl$_3$) δ 7.55 (s, 1H), 3.97 (s, 3H), 3.10-2.91 (m, 6H), 2.74 (dd, 1H), 1.31 (d, 3H) ppm.

6) 3-Chloro-2-methoxy-5-methyl-6,7,8,9-tetrahydro-5H-pyrido[2,3-d]azepine

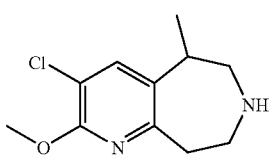

A mixture of 2-methoxy-5-methyl-7-(trifluoroacetyl)-6,7,8,9-tetrahydro-5H-pyrido[2,3-d]azepine (100 mg, 347 μmol), PCl$_5$ (722 mg, 3.47 mmol) and POCl$_3$ (10 ml) was heated at 125° C. in a sealed tube for 16 h. The reaction mixture was parted between DCM and sat. aq. NaHCO$_3$. The organic phase was washed with brine, dried over Na$_2$SO$_4$ and concentrated in vacuo. Chromatographic purification rendered 23.5 mg (21%) of 3-chloro-2-methoxy-5-methyl-7-(trifluoroacetyl)-6,7,8,9-tetrahydro-5H-pyrido[2,3-d]azepine. A mixture of 3-chloro-2-methoxy-5-methyl-7-(trifluoroacetyl)-6,7,8,9-tetrahydro-5H-pyrido[2,3-d]azepine (23.5 mg, 72.8 μmol) and K$_2$CO$_3$ (30 mg) in MeOH (7 ml) was heated at reflux for 2 h. The reaction mixture was concentrated in vacuo and chromatographic purification of the resulting residue rendered 11.2 mg (68%) of 3-chloro-2-methoxy-5-methyl-6,7,8,9-tetrahydro-5H-pyrido[2,3-d]azepine. $^1$H-NMR (CDCl$_3$) δ 7.48 (s, 1H), 3.99 (s, 3H), 3.55-3.30 (m, 4H), 3.25 (m, 1H), 3.07 (m, 1H), 2.85 (dd, 1H), 1.43 (d, 3H) ppm.

7) 3-Bromo-5-methyl-6,7,8,9-tetrahydro-5H-pyrido[2,3-d]azepin-2-ol

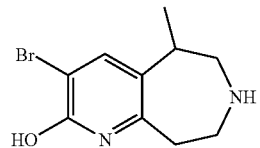

3-Bromo-2-methoxy-5-methyl-6,7,8,9-tetrahydro-5H-pyrido[2,3-d]azepine (152 mg, 414 μmol) in 48% aq. HBr (50 ml) was heated at reflux for 1 h. After neutralization with Na$_2$CO$_3$ and concentration in vacuo, the residue was purified by column chromatography and furnished 13.3 mg (13%) of 3-bromo-5-methyl-6,7,8,9-tetrahydro-5H-pyrido[2,3-d]azepin-2-ol. $^1$H-NMR (CDCl$_3$) δ 7.68 (s, 1H), 3.08-2.77 (m, 7H), 1.26 (d, 3H) ppm.

8) 3-Iodo-5-methyl-6,7,8,9-tetrahydro-5H-pyrido[2,3-d]azepin-2-ol

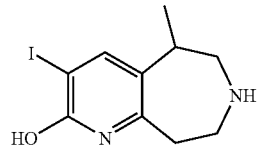

To a solution of 5-methyl-6,7,8,9-tetrahydro-5H-pyrido[2,3-d]azepin-2-ol hydrobromide (1.76 g, 6.79 mmol) in DCM (50 ml) and DMF (10 ml) was added Et$_3$N (2.90 ml, 20.7 mmol) and TFAA (1.00 ml, 6.90 mmol). The mixture was stirred for 2 h at ambient temperature, concentrated in vacuo and parted between sat. aq. NaHCO$_3$ and EtOAc. The organic phase was dried, concentrated in vacuo and purified by column chromatography to yield 1.46 g (77%) of 5-methyl-7-(trifluoroacetyl)-6,7,8,9-tetrahydro-5H-pyrido[2,3-d]azepin-2-ol. $^1$H-NMR (DMSO-d$_6$) δ 11.43 (br s, 1H), 7.30 (m, 1H), 6.18 (m, 1H), 3.95-3.42 (m, 4H), 3.06-2.96 (m, 2H), 2.95-2.87 (m, 1H), 1.12 (2× d, 3H) ppm. A mixture of 5-methyl-7-(trifluoroacetyl)-6,7,8,9-tetrahydro-5H-pyrido[2,3-d]azepin-2-ol (1.36 g, 4.96 mmol) and NIS (1.12 g, 4.96 mmol) in TFA (2 ml) and AcOH (36 ml) was stirred at room temperature for 16 h. Evaporation of TFA and AcOH followed by chromatographic purification of the resulting residue gave 1.95 g (98%) of 3-iodo-5-methyl-7-(trifluoroacetyl)-6,7,8,9-tetrahydro-5H-pyrido[2,3-d]azepin-2-ol. $^1$H-NMR (CDCl$_3$) δ 7.86 (s, 1H), 4.17-3.41 (m, 4H), 3.20-2.94 (m, 3H), 1.26 (2× d, 3H) ppm. A mixture of 3-iodo-5-methyl-7-(trifluoroacetyl)-6,7,8,9-tetrahydro-5H-pyrido[2,3-d]azepin-2-ol (50.0 mg, 125 μmol) and K$_2$CO$_3$ (17.3 mg, 125 μmol) in MeOH (10 ml) was heated at reflux for 4 h. The reaction mixture was concentrated in vacuo and purified by column chromatography rendering 20.2 mg (53%) of 3-iodo-5-methyl-6,7,8,9-tetrahydro-5H-pyrido[2,3-d]azepin-2-ol.
¹H-NMR (CDCl₃) δ 7.90 (s, 1H), 3.09-2.80 (m, 7H), 1.28 (d, 3H) ppm.

9) 2-Chloro-3-iodo-5-methyl-6,7,8,9-tetrahydro-5H-pyrido[2,3-d]azepine

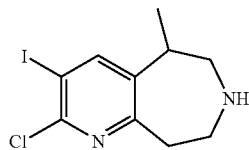

A mixture of 3-iodo-5-methyl-7-(trifluoroacetyl)-6,7,8,9-tetrahydro-5H-pyrido[2,3-d]azepin-2-ol (137 mg, 342 µmol), DMF (100 µl) and POCl₃ (5 ml) was heated at 100° C. for 16 h. The reaction mixture was concentrated in vacuo and purified by column chromatography to furnish 57.0 mg (40%) of 2-chloro-3-iodo-5-methyl-7-(trifluoroacetyl)-6,7,8,9-tetrahydro-5H-pyrido[2,3-d]azepine. MS (ESI) m/z 419.1/421.1. A mixture of 2-chloro-3-iodo-5-methyl-7-(trifluoroacetyl)-6,7,8,9-tetrahydro-5H-pyrido[2,3-d]azepine (58.0 mg, 139 µmol), K₂CO₃ (50 mg) and MeOH (10 ml) was heated for 1 h at 60° C. The reaction mixture was concentrated in vacuo and purified by column chromatography furnishing 37.7 mg (84%) of 2-chloro-3-iodo-5-methyl-6,7,8,9-tetrahydro-5H-pyrido[2,3-d]azepine. ¹H-NMR (CDCl₃) δ 7.86 (s, 1H), 3.13 (m, 2H), 3.07-2.92 (m, 4H), 2.75 (dd, 1H), 1.33 (d, 3H) ppm.

10) 3-Iodo-2-methoxy-5-methyl-6,7,8,9-tetrahydro-5H-pyrido[2,3-d]azepine

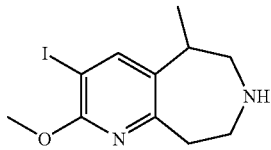

A mixture of 3-iodo-5-methyl-7-(trifluoroacetyl)-6,7,8,9-tetrahydro-5H-pyrido[2,3-d]azepin-2-ol (100 mg, 250 µmol), K₂CO₃ (200 mg), MeI (2 ml) and acetone (4 ml) was stirred for 16 h at ambient temperature. The reaction mixture was concentrated in vacuo and purified by column chromatography rendering 25.5 mg (25%) of 3-iodo-2-methoxy-5-methyl-7-(trifluoroacetyl)-6,7,8,9-tetrahydro-5H-pyrido[2,3-d]azepine and 41.9 mg (41%) of 3-iodo-1,5-dimethyl-7-(trifluoroacetyl)-1,5,6,7,8,9-hexahydro-2H-pyrido[2,3-d]azepin-2-one. ¹H-NMR of O-methylated product (CDCl₃) δ 7.79 (2× s, 1H), 3.95 (2× s, 3H), 3.94-3.78 (br m, 2H), 3.59 (br m, 1H), 3.56-3.36 (br m, 1H), 3.22 (m, 1H), 3.08 (br m, 2H), 1.30 (2× d, 3H) ppm. ¹H-NMR N-methylated product (CDCl₃) δ 7.80 (s, 1H), 3.97-3.65 (br m, 3H), 3.68 (2× s, 3H), 3.44-3.01 (m, 4H), 1.30 (2× d, 3H) ppm. A mixture of 3-iodo-2-methoxy-5-methyl-7-(trifluoroacetyl)-6,7,8,9-tetrahydro-5H-pyrido[2,3-d]azepine (25.5 mg, 62.0 µmol), K₂CO₃ (17.0 mg, 124 µmol) and MeOH (7 ml) was heated for 5 h at 60° C.

The reaction mixture was concentrated in vacuo and purified by column chromatography to furnish 5.90 mg (30%) of 3-iodo-2-methoxy-5-methyl-6,7,8,9-tetrahydro-5H-pyrido[2,3-d]azepine. ¹H-NMR (DMSO-d₆) δ 7.84 (s, 1H), 3.83 (s, 3H), 3.00-2.90 (m, 3H), 2.86-2.77 (m, 3H), 2.65 (dd, 1H), 1.21 (d, 3H) ppm.

11) 3-Iodo-1,5-dimethyl-1,5,6,7,8,9-hexahydro-2H-pyrido[2,3-d]azepin-2-one

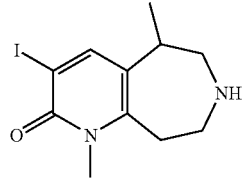

A mixture of 3-iodo-1,5-dimethyl-7-(trifluoroacetyl)-1,5,6,7,8,9-hexahydro-2H-pyrido[2,3-d]azepin-2-one (41.9 mg, 101 µmol), K₂CO₃ (28.0 mg, 202 µmol) and MeOH (8 ml) was heated for 5 h at 60° C. The reaction mixture was concentrated in vacuo and purified by column chromatography to furnish 17.8 mg (55%) of 3-iodo-1,5-dimethyl-1,5,6,7,8,9-hexahydro-2H-pyrido[2,3-d]azepin-2-one. ¹H-NMR (DMSO-d₆) δ 7.83 (s, 1H), 3.57 (s, 3H), 2.99 (m, 2H), 2.87 (ddd, 1H), 2.78 (m, 3H), 2.47 (dd, 1H), 1.15 (d, 3H) ppm.

12) 2-(Allyloxy)-3-iodo-5-methyl-6,7,8,9-tetrahydro-5H-pyrido[2,3-d]azepine

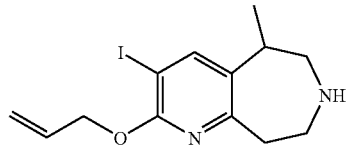

A mixture of 3-iodo-5-methyl-7-(trifluoroacetyl)-6,7,8,9-tetrahydro-5H-pyrido[2,3-d]azepin-2-ol (615 mg, 1.54 mmol), allyl bromide (1.33 ml, 15.4 mmol), Ag₂CO₃ (504 mg, 1.83 mmol) and CHCl₃ (35 ml) was stirred under exclusion of light for 4 d at ambient temperature. The reaction mixture was diluted with EtOAc (100 ml) and filtered. The filtrate was concentrated in vacuo and purified by column chromatography rendering 445 mg (66%) of 2-(allyloxy)-3-iodo-5-methyl-7-(trifluoroacetyl)-6,7,8,9-tetrahydro-5H-pyrido[2,3-d]azepine. ¹H-NMR (CDCl₃) δ 7.82 (2×s, 1H), 6.18 (dddd, 1H), 5.48 (m, 1H), 5.27 (m, 1H), 4.87 (m, 2H), 4.16-3.01 (m, 7H), 1.32 (2× d, 3H) ppm. A mixture of 2-(allyloxy)-3-iodo-5-methyl-7-(trifluoroacetyl)-6,7,8,9-tetrahydro-5H-pyrido[2,3-d]azepine (145 mg, 329 µmol), K₂CO₃ (150 mg) and MeOH (6 ml) was heated for 1 h at 60° C. The reaction mixture was concentrated in vacuo and purified by column chromatography to give 56.3 mg (50%) of 2-(allyloxy)-3-iodo-5-methyl-6,7,8,9-tetrahydro-5H-pyrido[2,3-d]azepine. ¹H-NMR (CDCl₃) δ 7.78 (s, 1H), 6.08 (dddd, 1H), 5.46 (ddd, 1H), 5.25 (ddd, 1H), 4.86 (m, 2H), 3.20-3.02 (m, 5H), 2.98 (m, 1H), 2.78 (m, 1H), 1.33 (d, 3H) ppm.

13) 3,5-Dimethyl-6,7,8,9-tetrahydro-5H-furo[3',2':5,6]pyrido[2,3-d]azepine

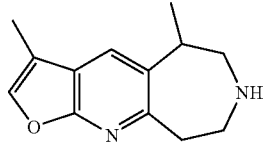

A mixture of 2-(allyloxy)-3-iodo-5-methyl-7-(trifluoroacetyl)-6,7,8,9-tetrahydro-5H-pyrido[2,3-d]azepine (300 mg, 682 µmol), Pd(PPh$_3$)$_2$Cl$_2$ (120 mg, 170 µmol), NaOAc (168 mg, 2.04 mmol) and DMA (20 ml) was heated for 30 min at 125° C. The reaction mixture was concentrated in vacuo and purified by column chromatography to give 68.0 mg (32%) of 3,5-dimethyl-7-(trifluoroacetyl)-6,7,8,9-tetrahydro-5H-furo[3',2':5,6]pyrido[2,3-d]azepine. H-NMR (CDCl$_3$) δ 7.68 (2× s, 1H), 7.46 (2× s, 1H), 4.25-3.25 (m, 7H), 2.24 (2× d, 3H), 1.44 (2×d, 3H) ppm. A mixture of 3,5-dimethyl-7-(trifluoroacetyl)-6,7,8,9-tetrahydro-5H-furo[3',2':5,6]pyrido[2,3-d]azepine (62.0 mg, 199 µmol), K$_2$CO$_3$ (80 mg) and MeOH (6 ml) was heated for 1 h at 60° C. The reaction mixture was concentrated in vacuo and purified by column chromatography to give 19.6 mg (46%) of 3,5-dimethyl-6,7,8,9-tetrahydro-5H-furo[3',2':5,6]pyrido[2,3-d]azepine. $^1$H-NMR (CDCl$_3$) δ 7.69 (s, 1H), 7.47 (d, 1H), 3.63-3.33 (m, 5H), 3.06 (t, 1H), 2.87 (t, 1H), 2.25 (d, 3H), 1.54 (d, 3H) ppm.

14) 2-Chloro-5-methyl-6,7,8,9-tetrahydro-5H-pyrido[2,3-d]azepine

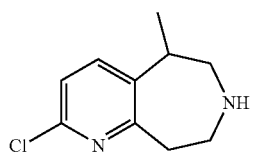

A mixture of 5-methyl-7-(trifluoroacetyl)-6,7,8,9-tetrahydro-5H-pyrido[2,3-d]azepin-2-ol (100 mg, 365 µmol), DMF (50 µl) and POCl$_3$ (5 ml) was heated at 100° C. for 3 h. The reaction mixture was concentrated in vacuo and purified by column chromatography rendering 101 mg (94%) of 2-chloro-5-methyl-7-(trifluoroacetyl)-6,7,8,9-tetrahydro-5H-pyrido[2,3-d]azepine. MS (ESI) m/z 293.2/295.2. A mixture of 2-chloro-5-methyl-7-(trifluoroacetyl)-6,7,8,9-tetrahydro-5H-pyrido[2,3-d]azepine (40.0 mg, 137 µmol), K$_2$CO$_3$ (80.0 mg) and MeOH (5 ml) was heated for 2 h at 70° C. The reaction mixture was concentrated in vacuo and purified by column chromatography furnishing 6.0 mg (22%) of 2-chloro-5-methyl-6,7,8,9-tetrahydro-5H-pyrido[2,3-d]azepine. $^1$H-NMR (CDCl$_3$) δ. $^1$H-NMR (CDCl$_3$) δ 7.48 (d, 1H), 7.91 (d, 1H), 3.58 (s, 3H), 3.55-3.20 (m, 5H), 2.93 (dd, 1H), 2.73 (dd, 1H), 1.43 (d, 3H) ppm.

15) 3-Bromo-2-chloro-5-methyl-6,7,8,9-tetrahydro-5H-pyrido[2,3-d]azepine

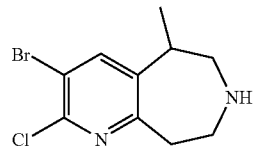

TFAA (2.5 ml) and Et$_3$N (20 ml) was added to a solution of 3-bromo-5-methyl-6,7,8,9-tetrahydro-5H-pyrido[2,3-d]azepin-2-ol (426 mg, 1.66 mmol) in DCM (60 ml). The mixture was stirred for 1 h at ambient temperature, concentrated in vacuo and parted between NaHCO$_3$ and EtOAc. The organic phase was dried, concentrated and purified by column chromatography to yield 629 mg (93%) of 3-bromo-5-methyl-7-(trifluoroacetyl)-6,7,8,9-tetrahydro-5H-pyrido[2,3-d]azepin-2-ol. MS (ESI) m/z 353.2/355.1. A mixture of 3-bromo-5-methyl-7-(trifluoroacetyl)-6,7,8,9-tetrahydro-5H-pyrido[2,3-d]azepin-2-ol (629 mg, 1.78 mmol), DMF (1 ml) and POCl$_3$ (10 ml) was heated at 100° C. for 13 h. The reaction mixture was concentrated in vacuo and purified by column chromatography rendering 185 mg (28%) of 3-bromo-2-chloro-5-methyl-7-(trifluoroacetyl)-6,7,8,9-tetrahydro-5H-pyrido[2,3-d]azepine. $^1$H-NMR (CDCl$_3$) δ 7.72 (s, 1H), 4.30-3.05 (m, 7H), 1.38 (d, 1.2H), 1.35 (d, 1.8H). A mixture of 3-bromo-2-chloro-5-methyl-7-(trifluoroacetyl)-6,7,8,9-tetrahydro-5H-pyrido[2,3-d]azepine (79.0 mg, 213 µmol), N$_2$H$_4$H$_2$O (91.0 µl, 1.47 mmol) and EtOH (30 ml) was stirred for 16 h at room temperature. The reaction mixture was parted between EtOAc and sat. aq. NaHCO$_3$. The organic phase was dried over Na$_2$SO$_4$ and concentrated in vacuo. Chromatographic purification rendered 45.0 mg (76%) of 3-bromo-2-chloro-5-methyl-6,7,8,9-tetrahydro-5H-pyrido[2,3-d]azepine. $^1$H-NMR (CDCl$_3$) δ 7.64 (s, 1H), 3.16 (m, 2H), 3.05 (m, 3H), 2.92 (m, 1H), 2.72 (dd, 1H), 1.33 (d, 3H) ppm.

16) 2-Methoxy-5-methyl-3-vinyl-6,7,8,9-tetrahydro-5H-pyrido[2,3-d]azepine

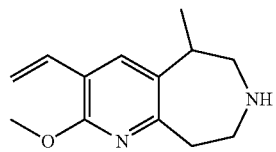

A mixture of 3-bromo-2-methoxy-5-methyl-7-(trifluoroacetyl)-6,7,8,9-tetrahydro-5H-pyrido[2,3-d]azepine (220 mg, 599 µmol), Bu$_3$SnCH=CH$_2$ (523 µl, 1.79 mmol), Pd(PPh$_3$)$_4$ (50 mg), and toluene (10 ml) was heated in a sealed tube at 110° C. for 16 h. The solvent was evaporated and the resulting residue was purified by column chromatography to render 165 mg (88%) of 2-methoxy-5-methyl-7-(trifluoroacetyl)-3-vinyl-6,7,8,9-tetrahydro-5H-pyrido[2,3-d]azepine. A mixture of 2-methoxy-5-methyl-7-(trifluoroacetyl)-3-vinyl-6,7,8,9-tetrahydro-5H-pyrido[2,3-d]azepine (32 mg, 102 µmol), K$_2$CO$_3$ (40 mg), MeOH (5 ml) and H$_2$O (1 ml) was heated to reflux for 10 min. The reaction mixture was concentrated in vacuo and the resulting residue was purified by column chromatography to yield 17.0 mg (77%) of 2-methoxy-5-methyl-3-vinyl-6,7,8,9-tetrahydro-5H-pyrido[2,3-d]azepine. $^1$H-NMR (CDCl$_3$) δ 7.58 (s, 1H), 6.92 (dd, 1H), 5.86 (d, 1H), 5.40 (d, 1H), 4.02 (s, 3H), 3.60-3.40 (m, 4H), 3.31 (m, 1H), 3.18 (dd, 1H), 3.00 (m, 1H), 1.52 (d, 3H) ppm.

17) 3-Ethyl-2-methoxy-5-methyl-6,7,8,9-tetrahydro-5H-pyrido[2,3-d]azepine

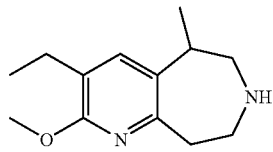

A mixture of 2-methoxy-5-methyl-7-(trifluoroacetyl)-3-vinyl-6,7,8,9-tetrahydro-5H-pyrido[2,3-d]azepine (52 mg, 166 μmol), 5% Pd/C (20 mg), and MeOH (20 ml) was stirred under H$_2$ (1 atm) for 15 h. Filtration and concentration of the filtrate in vacuo yielded 36.0 mg (69%) of 3-ethyl-2-methoxy-5-methyl-7-(trifluoroacetyl)-6,7,8,9-tetrahydro-5H-pyrido[2,3-d]azepine. MS (ESI) m/z 317.3. A mixture of 3-ethyl-2-methoxy-5-methyl-7-(trifluoroacetyl)-6,7,8,9-tetrahydro-5H-pyrido[2,3-d]azepine (36.0 mg, 114 μmol), K$_2$CO$_3$ (100 mg), MeOH (5 ml) and H$_2$O (1 ml) was heated to reflux for 10 min. The reaction mixture was concentrated in vacuo and the resulting residue was purified by column chromatography to yield 10.2 mg (40%) of 3-ethyl-2-methoxy-5-methyl-6,7,8,9-tetrahydro-5H-pyrido[2,3-d]azepine.
$^1$H-NMR (MeOH-d$_4$) δ 7.30 (s, 1H), 3.89 (s, 3H), 3.17 (m, 5H), 3.06 (m, 1H), 2.87 (m, 1H), 2.57 (m, 2H), 1.31 (d, 3H), 1.15 (t, 3H) ppm.

18) 2-(Difluoromethoxy)-5-methyl-6,7,8,9-tetrahydro-5H-pyrido[2,3-d]azepine

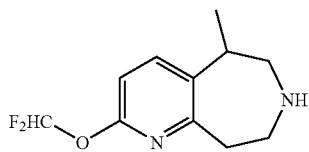

To a mixture of 5-methyl-7-(trifluoroacetyl)-6,7,8,9-tetrahydro-5H-pyrido[2,3-d]azepin-2-ol (77.0 mg, 281 μmol), K$_2$CO$_3$ (19.0 mg, 141 μmol) and DMF (1.4 ml) was added F$_2$ClCCO$_2$Na (47.0 mg, 310 μmol). The mixture was heated at 90° C. for 2 h. The reaction mixture was parted between sat. aq. NaHCO$_3$ and EtOAc. The organic layer was dried, concentrated in vacuo and purified by means of column chromatography to give 49.0 mg (54%) of 2-(difluoromethoxy)-5-methyl-7-(trifluoroacetyl)-6,7,8,9-tetrahydro-5H-pyrido[2,3-d]azepine. MS (ESI) m/z 325.2. A mixture of 2-(difluoromethoxy)-5-methyl-7-(trifluoroacetyl)-6,7,8,9-tetrahydro-5H-pyrido[2,3-d]azepine (28.0 mg, 86.0 μmol), K$_2$CO$_3$ (30 mg), MeOH (1 ml) and H$_2$O (200 μl) was heated to reflux for 10 min. The reaction mixture was concentrated in vacuo and the resulting residue was purified by column chromatography to yield 7.0 mg (36%) of 2-(difluoromethoxy)-5-methyl-6,7,8,9-tetrahydro-5H-pyrido[2,3-d]azepine.
$^1$H-NMR (CDCl$_3$) δ 7.46 (d, 1H), 6.66 (d, 1H), 3.09 (m, 2H), 3.40-2.90 (m, 4H), 2.74, (dd, 1H), 1.31 (d, 3H) ppm.

19) 3-Bromo-N,5-dimethyl-6,7,8,9-tetrahydro-5H-pyrido[2,3-d]azepin-2-amine

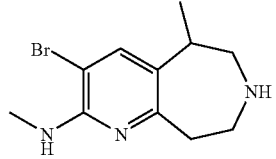

A mixture of 3-bromo-5-methyl-7-(trifluoroacetyl)-6,7,8,9-tetrahydro-5H -pyrido[2,3-d]azepin-2-ol (30.0 mg, 85.0 μmol), Tf$_2$O (50 μl), K$_2$CO$_3$ (18 mg) and DCM (1 ml) was stirred for 16 h at room temperature. The mixture was extracted with sat. aq. NaHCO$_3$, dried over Na$_2$SO$_4$, concentrated in vacuo and purified by column chromatography to yield 11.0 mg (26%) of 3-bromo-5-methyl-7-(trifluoroacetyl)-6,7,8,9-tetrahydro-5H-pyrido[2,3-d]azepin-2-yl trifluoromethanesulfonate. A mixture of methylamine (50 μl), 3-bromo-5-methyl-7-(trifluoroacetyl)-6,7,8,9-tetrahydro-5H-pyrido[2,3-d]azepin-2-yl trifluoromethanesulfonate (11.0 mg, 22.7 μmol), and THF (1 ml) was heated to reflux for 15 h. The reaction mixture was parted between sat. aq. NaHCO$_3$ and EtOAc. The organic layer was dried, concentrated in vacuo and purified with column chromatography to give 5.2 mg (62%) of 3-bromo-N,5-dimethyl-7-(trifluoroacetyl)-6,7,8,9-tetrahydro-5H-pyrido[2,3-d]azepin-2-amine. MS (ESI) m/z 486.2 (M+H$^+$). A mixture of 3-bromo-N,5-dimethyl-7-(trifluoroacetyl)-6,7,8,9-tetrahydro-5H-pyrido[2,3-d]azepin-2-amine (5.2 mg, 14.2 μmol), K$_2$CO$_3$ (15 mg), MeOH (1 ml) and H$_2$O (100 μl) was heated to reflux for 10 min. The reaction mixture was concentrated in vacuo and the resulting residue was purified by column chromatography to yield 2.1 mg (55%) of 3-bromo-N,5-dimethyl-6,7,8,9-tetrahydro-5H-pyrido[2,3-d]azepin-2-amine. MS (ESI) m/z 271.2 (M+H$^+$).

20) 2-Methoxy-5-methyl-3-nitro-6,7,8,9-tetrahydro-5H-pyrido[2,3-d]azepine

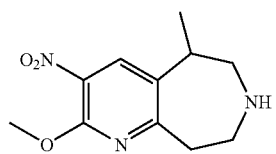

Nitric Acid (200 μl) was added dropwise to a stirred solution of 2-methoxy-5-methyl-7-(trifluoroacetyl)-6,7,8,9-tetrahydro-5H-pyrido[2,3-d]azepine (174 mg, 604 μmol) in H$_2$SO$_4$ (1.5 ml). The reaction mixture was added into cold water after 3 d of stirring at room temperature. K$_2$CO$_3$ was added to neutralize the mixture to pH=8. After extraction with EtOAc, the organic layer was dried over Na$_2$SO$_4$, concentrated in vacuo and purified by column chromatography to give 155 mg (77%) of 2-methoxy-5-methyl-3-nitro-7-(trifluoroacetyl)-6,7,8,9-tetrahydro-5H-pyrido[2,3-d]azepine. MS (ESI) m/z 334. After treatment of 2-methoxy-5-methyl-3-nitro-7-(trifluoroacetyl)-6,7,8,9-tetrahydro-5H-pyrido[2, 3-d]azepine (30.0 mg, 90.0 µmol) with K$_2$CO$_3$ (30 mg), methanol (1 ml) and H$_2$O (0.2 ml) at 60° C. for 10 minutes, the reaction was quenched with sat. aq. NH$_4$Cl and extracted with DCM. The organic layer was dried over Na$_2$SO$_4$, concentrated in vacuo and purified by column chromatography to give 21 mg (99%) of 2-methoxy-5-methyl-3-nitro-6,7,8,9-tetrahydro-5H-pyrido[2,3-d]azepine. $^1$H-NMR (CDCl$_3$) δ 8.10 (s, 1H), 4.09 (s, 3H), 3.25 (m, 2H), 3.10 (m, 3H), 2.93 (dd, 1H), 2.72 (dd, 1H), 1.39 (d, 3H) ppm.

21) 2-Methoxy-5-methyl-6,7,8,9-tetrahydro-5H-pyrido[2,3-d]azepin-3-amine

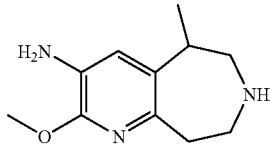

The nitro group of 2-methoxy-5-methyl-3-nitro-7-(trifluoroacetyl)-6,7,8,9-tetrahydro-5H-pyrido[2,3-d]azepine (40.0 mg, 120 µmol) of was reduced with 10% Pd/C in EtOH (5 ml) under H2 (1 attn). After 2 h of stirring at room temperature, the reaction mixture was filtered through a pad of Celite and rinsed with MeOH. 2-methoxy-5-methyl-7-(trifluoroacetyl)-6,7,8,9-tetrahydro-5H-pyrido[2,3-d]azepin-3-amine (35 mg, 96%) was obtained after removal of solvent. MS (ESI) m/z 304. Removal of the trifluoroacetyl group was carried out as described above and gave 21.0 mg (88%) of 2-methoxy-5-methyl-6,7,8,9-tetrahydro-5H-pyrido[2,3-d]azepin-3-amine. $^1$H-NMR (CDCl$_3$) δ 6.72 (s, 1H), 3.93 (s, 3H), 3.20-2.80 (m, 6H), 2.74 (dd, 1H), 2.76 (1H), 1.28 (d, 3 H) ppm.

22) 2-Methoxy-N,N,5-trimethyl-6,7,8,9-tetrahydro-5H-pyrido[2,3-d]azepin-3-amine

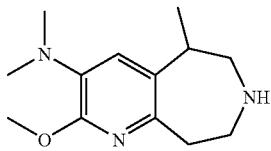

NaBH$_3$CN (63.0 mg, 990 µmol) was added portionwise at room temperature to a solution of 2-methoxy-5-methyl-7-(trifluoroacetyl)-6,7,8,9-tetrahydro-5H-pyrido[2,3-d] azepin-3-amine (100 mg, 330 µmol) and HCHO (37% in H$_2$O, 2.31 mmol) in MeCN (1 ml). The mixture was stirred at room temperature for 15 min before slow addition of HOAc (0.2 ml). The reaction was stirred at room temperature for an additional 3 h and was basified with aq. K$_2$CO$_3$ and extracted with DCM. The organic layer was washed with water, dried over Na$_2$SO$_4$ and concentrated under reduced pressure. The crude product was purified by column chromatography to provide 94.0 mg (86%) of 2-methoxy-N,N,5-trimethyl-7-(trifluoroacetyl)-6,7,8,9-tetrahydro-5H-pyrido[2,3-d]azepin-3-amine. MS (ESI) m/z 332. 2-Methoxy-N,N,5-trimethyl-7-(trifluoroacetyl)-6,7,8,9-tetrahydro-5H-pyrido[2,3-d] azepin-3-amine (35.0 mg, 106 µmol) was treated under basic condition (K$_2$CO$_3$/MeOH/H$_2$O), as described above, to provide 17 mg (68%) of 2-methoxy-N,N,5-trimethyl-6,7,8,9-tetrahydro-5H-pyrido[2,3-d]azepin-3-amine. MS (ESI) m/z 236.

23) 4-Bromo-2-methoxy-5-methyl-6,7,8,9-tetrahydro-5H-pyrido[2,3-d]azepin-3-amine

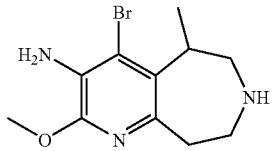

A solution of NBS (1.16 g, 6.50 mmol) in DCM (40 ml) was added dropwise to a stirred and cooled (0-5° C.) solution of 2-methoxy-5-methyl-7-(trifluoroacetyl)-6,7,8,9-tetrahydro-5H-pyrido[2,3-d]azepin-3-amine (1.97 g, 6.50 mmol) in DCM (40 ml) over a period of 20 min. After 30 minutes of stirring, the reaction was quenched with sat. aq. NaHCO$_3$ and extracted with DCM. The organic layer was dried, concentrated in vacuo and purified by column chromatography to provide 920 mg (37%) of 4-bromo-2-methoxy-5-methyl-7-(trifluoroacetyl)-6,7,8,9-tetrahydro-5H-pyrido[2,3-d] azepin-3-amine. $^1$H-NMR (CDCl$_3$) δ 4.36 (0.5H), 4.18 (2H), 4.00 (0.5H), 3.95 (3H), 3.79 (1H), 3.74 (1H), 3.70 (1H), 3.38 (1H), 3.23 (1H), 3.07 (1H), 1.19 (3H) ppm. 4-Bromo-2-methoxy-5-methyl-7-(trifluoroacetyl)-6,7,8,9-tetrahydro-5H-pyrido[2,3-d]azepin-3-amine (57.0 mg, 0.15 mmol) of was deprotected using K$_2$CO$_3$ (62 mg, 0.45 mmol), MeOH (2.3 ml) and H$_2$O (0.5 ml) at 55-60° C. for 30 minutes. After carefully removing MeOH under reduced pressure, the mixture was diluted with aq. NaHCO$_3$ and extracted with DCM. The organic layer was dried over Na$_2$SO$_4$ and concentrated in vacuo to give 37.0 mg (86%) of 4-bromo-2-methoxy-5-methyl-6,7,8,9-tetrahydro-5H-pyrido[2,3-d]azepin-3-amine. $^1$H-NMR (CDCl$_3$) δ 3.96 (s, 3H), 3.54 (m, 1H), 3.26 (dd, 2H), 3.18 (dd, 1H), 3.02 (d, 1H), 2.94 (dd, 1H), 2.78 (dd, 1H), 1.32 (d, 3H) ppm.

24) N-Ethyl-2-methoxy-5-methyl-6,7,8,9-tetrahydro-5H-pyrido[2,3-d]azepin-3-amine

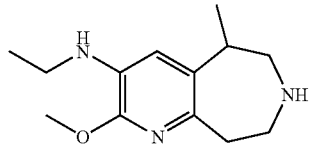

A mixture of 2-methoxy-5-methyl-7-(trifluoroacetyl)-6,7, 8,9-tetrahydro-5H -pyrido[2,3-d]azepin-3-amine (455 mg, 1.5 mmol), acetaldehyde (253 µl, 4.50 mmol) and 5% Pd/C (23.0 mg) in EtOH (18 ml) was subjected to H2 (50 psi) for 16 h at room temperature. The reaction mixture was filtered, concentrated under reduced pressure and purified by column chromatography to provide 280 mg (56%) of N-ethyl-2-methoxy-5-methyl-7-(trifluoroacetyl)-6,7,8,9-tetrahydro-5H-pyrido[2,3-d]azepin-3-amine. $^1$H NMR (CDCl$_3$) δ 6.47 (1H), 4.03 (0.5H), 3.88 (5H), 3.71 (0.5H), 3.43 (1H), 3.64 (3H), 2.98 (2H), 1.20 (6H) ppm. A mixture of of N-ethyl-2-methoxy-5-methyl-7-(trifluoroacetyl)-6,7,8,9-tetrahydro-5H-pyrido[2,3-d]azepin-3-amine (331 mg, 1.00 mmol), K₂CO₃ (415 mg, 3.00 mmol), MeOH (13 ml) and H20 (2.7 ml) was stirred for 16h at room temperature. After removal of solvent under reduced pressure, the mixture was taken into aq. NaHCO₃ and extracted with DCM. The organic layer was dried and concentrated in vacuo to give 204 mg (87%) of N-ethyl-2-methoxy-5-methyl-6,7,8,9-tetrahydro-5H-pyrido[2,3-d]azepin-3-amine. ¹H-NMR (CDCl₃) δ 6.48 (s, 1H), 3.87 (s, 3H), 3.80 (br s, 1H), 3.10-2.70 (m, 9H), 2.48 (br s, 1H), 1.26 (d, 3H), 1.24 (t, 3H) ppm.

25) 4-Chloro-N-ethyl-2-methoxy-5-methyl-6,7,8,9-tetrahydro-5H-pyrido[2,3-d]azepin-3-amine

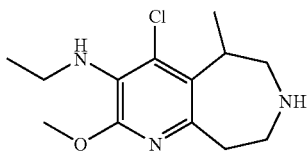

To a solution of N-ethyl-2-methoxy-5-methyl-7-(trifluoroacetyl)-6,7,8,9-tetrahydro-5H-pyrido[2,3-d]azepin-3-amine (99.0 mg, 0.30 mmol) in MeCN (5 ml) was added NCS (44.0 mg, 0.33 mmol) at room temperature and the mixture was refluxed for 30 minutes. The reaction was quenched with excess of sat. aq. NaHCO₃ and extracted with EtOAc. The organic layer was dried over Na₂SO₄, concentrated in vacuo and purified by column chromatography to give 40 mg (36%) of 4-chloro-N-ethyl-2-methoxy-5-methyl-7-(trifluoroacetyl)-6,7,8,9-tetrahydro-5H-pyrido[2,3-d]azepin-3-amine. ¹H-NMR (CDCl₃) δ 4.39 (0.5H), 4.04 (0.5H), 3.94 (3H), 3.83 (1H), 3.78 (1H), 3.72 (1H), 3.45 (1H), 3.35 (2H), 3.25 (1H), 3.09 (1H), 1.19 (6H) ppm. A mixture of 4chloro-N-ethyl-2-methoxy-5-methyl-7-(trifluoroacetyl)-6,7,8,9-tetrahydro-5H-pyrido[2,3-d]azepin-3-amine (37.0 mg, 0.10 mmol), K₂CO₃ (40 mg), MeOH (1.5 ml) and H₂O (0.3 ml) was stirred for 16 h at room temperature. After removal of solvent under reduced pressure, the mixture was taken into aq. NaHCO₃ and extracted with DCM. The organic layer was dried and concentrated in vacuo to give 27 mg (93%) of 4-chloro-N-ethyl-2-methoxy-5-methyl-6,7,8,9-tetrahydro-5H-pyrido[2,3-d]azepin-3-amine. ¹H-NMR (CDCl₃) δ 3.85 (s, 3H), 3.47 (m, 1H), 3.23 (m, 2H), 3.16 (m, 2H), 3.08 (m, 1H), 2.89 (dd, 2H), 2.69 (dd, 1H), 1.22 (d, 3H), 1.09 (t, 3H) ppm.

26) 3,4-Dibromo-2-methoxy-5-methyl-6,7,8,9-tetrahydro-5H-pyrido[2,3-d]azepine

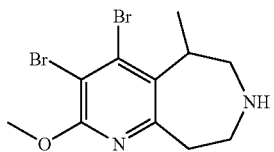

To a solution of CuBr₂ (0.64 g, 2.88 mmol) and ⁿBuNO₂ (0.42 ml, 3.6 mmol) in MeCN (14 ml) was added a solution of 4-bromo-2-methoxy-5-methyl-7-(trifluoroacetyl)-6,7,8,9-tetrahydro-5H-pyrido[2,3-d]azepin-3-amine (0.92 g, 2.41 mmol) in MeCN (10 ml) at room temperature. The reaction mixture was then stirred at 50° C. for 4 h. After removal of MeCN under reduced pressure, the reaction was quenched with sat. aq. NaHCO₃ and extracted with EtOAc. The organic layer was dried over Na₂SO₄, concentrated in vacuo and purified by column chromatography to give 813 mg (76%) of 3,4-dibromo-2-methoxy-5-methyl-7-(trifluoroacetyl)-6,7,8,9-tetrahydro-5H-pyrido[2,3-d]azepine. ¹H-NMR (CDCl₃) δ 4.31 (0.5H), 4.01 (0.5H), 3.91 (3H), 3.85 (1H), 3.69 (1H), 3.39 (1H), 3.23 (1H), 3.12 (1H), 3.06 (1H), 1.17 (3H) ppm. A mixture of 3,4-dibromo-2-methoxy-5-methyl-7-(trifluoroacetyl)-6,7,8,9-tetrahydro-5H-pyrido[2,3-d]azepine (803 mg, 1.80 mmol), K₂CO₃ (746 mg, 5.40 mmol), MeOH (32 ml) and H₂O (6 ml) was heated at 55-60° C. for 30 minutes. After removal of solvent under reduced pressure, the mixture was taken into aq. NaHCO₃ and extracted with DCM. The organic layer was dried and concentrated in vacuo to give 580 mg (92%) of 3,4-dibromo-2-methoxy-5-methyl-6,7,8,9-tetrahydro-5H-pyrido[2,3-d]azepine. ¹H-NMR (CDCl₃) δ 3.89 (s, 3H), 3.63 (m, 1H), 3.21 (m, 2H), 3.09 (dd, 1H), 2.94 (m, 2H), 2.72 (dd, 1H), 1.25 (d, 3H) ppm.

27) 3-Bromo-4-chloro-2-methoxy-5-methyl-6,7,8,9-tetrahydro-5H-pyrido[2,3-d]azepine

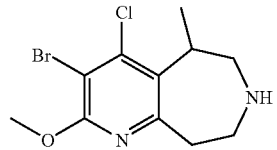

To a solution of 2-methoxy-5-methyl-7-(trifluoroacetyl)-6,7,8,9-tetrahydro-5H-pyrido[2,3-d]azepin-3-amine (303 mg, 1.00 mmol) in MeCN (6 ml) was added a solution of NCS (134 mg, 1.00 mmol) in MeCN (6 ml). The resulting mixture was stirred for 2 h at 50° C. and then quenched with excess of sat. aq. NaHCO₃ and extracted with EtOAc. The organic layer was dried over Na₂SO4, concentrated in vacuo and purified by column chromatography to give 165 mg (49%) of 4-chloro-2-methoxy-5-methyl-7-(trifluoroacetyl)-6,7,8,9-tetrahydro-5H-pyrido[2,3-d]azepin-3-amine. ¹H-NMR (CDCl₃) δ 4.28 (0.5H), 3.95 (2.5H), 3.88 (3H), 3.71 (2H), 3.61 (1H), 3.34 (1H), 3.16 (1H), 2.99 (1H), 1.13 (3H) ppm. To a solution of CuBr₂ (43.0 mg, 0.19 mmol) and ⁿBuNO₂ (28.0 μl, 0.24 mmol) in MeCN (2.7 ml) was added a solution of 4-chloro-2-methoxy-5-methyl-7-(trifluoroacetyl)-6,7,8,9-tetrahydro-5H-pyrido[2,3-d]azepin-3-amine (54.0 mg, 0.16 mmol) in MeCN (2 ml) at room temperature. After leaving the mixture for 16 h at room temperature, it was heated at 50° C. for 4 h. After removal of MeCN under reduced pressure, the reaction was quenched with sat. aq. NaHCO₃ and extracted with EtOAc. The organic layer was dried over Na₂SO₄, concentrated in vacuo and purified by column chromatography to give 45 mg (70%) of 3-bromo-4-chloro-2-methoxy-5-methyl-7-(trifluoroacetyl)-6,7,8,9-tetrahydro-5H-pyrido[2,3-d]azepine. ¹H NMR (CDCl₃) δ 4.29 (0.5H), 4.00 (0.5H), 3.90 (3H), 3.85 (1H), 3.75 (1H), 3.40 (1H), 3.30 (1H), 3.20 (1H), 3.10 (1H), 1.16 (3H) ppm. A mixture of 3-bromo-4-chloro-2-methoxy-5-methyl-7-(trifluoroacetyl)-6,7,8,9-tetrahydro-5H-pyrido[2,3-d]azepine (60 mg, 0.15 mmol), K₂CO₃ (62 mg, 0.45 mmol), MeOH (2.4 ml) and H₂O (0.5 ml) was heated at 55-60° C. for 1 h. After removal of solvent under reduced pressure, the mixture was taken into aq. NaHCO₃ and extracted with EtOAc. The organic layer was dried and concentrated in vacuo to give 45 mg (98%) of 3-bromo-4-chloro-2-methoxy-5-methyl-6,7,8,9-tetrahydro-5H-pyrido[2,3-d]

azepine. ¹H-NMR (CDCl₃) δ 3.89 (s, 3H), 3.58 (m, 1H), 3.22 (m, 2H), 3.09 (dd, 1H), 2.93 (m, 2H), 2.71 (dd, 1H), 1.24 (d, 3H) ppm.

28) 3,4-Dichloro-2-methoxy-5-methyl-6,7,8,9-tetrahydro-5H-pyrido[2,3-d]azepine

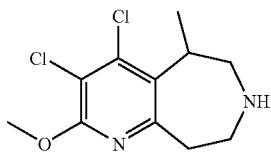

To a solution of CuCl₂ (87 mg, 0.65 mmol) and ″BuNO₂ (950 μl, 0.81 mmol) in MeCN (18 ml) was added a solution of 4-chloro-2-methoxy-5-methyl-7-(trifluoroacetyl)-6,7,8,9-tetrahydro-5H-pyrido[2,3-d]azepin-3-amine (182 mg, 0.54 mmol) in MeCN (9 ml) at room temperature. After heating the mixture at 50° C. for 4 h, it was quenched with sat. aq. NaHCO₃ and extracted with EtOAc The organic layer was dried over Na₂SO₄, concentrated in vacuo and purified by column chromatography to provide 62 mg (32%) of 3,4-dichloro-2-methoxy-5-methyl-7-(trifluoroacetyl)-6,7,8,9-tetrahydro-5H-pyrido[2,3-d]azepine. ¹H-NMR (CDCl₃) δ 4.30 (0.5H), 4.00 (0.5H), 3.92 (3H), 3.83 (1H), 3.74 (1H), 3.38 (1H), 3.25 (2H), 3.10 (1H), 1.16 (3H) ppm. A mixture of 3,4-dichloro-2-methoxy-5-methyl-7-(trifluoroacetyl)-6,7,8,9-tetrahydro-5H-pyrido[2,3-d]azepine (61 mg, 0.17 mmol), K₂CO₃ (70 mg, 0.51 mmol), MeOH (2.4 ml) and H₂O (0.5 ml) was heated at 55-60° C. for 30 minutes. After removal of solvent under reduced pressure, the mixture was taken into aq. NaHCO₃ and extracted with DCM. The organic layer was dried and concentrated in vacuo to give 40 mg (90%) of 3,4-dichloro-2-methoxy-5-methyl-6,7,8,9-tetrahydro-5H-pyrido[2,3-d]azepine. ¹H-NMR (CDCl₃) δ 3.91 (s, 3H), 3.55 (m, 1H), 3.20 (m, 2H), 3.10 (dd, 1H), 2.93 (m, 2H), 2.71 (dd, 1H), 1.25 (d, 3H) ppm.

29) 5-Methyl-6,7,8,9-tetrahydro-5H-pyrido[2,3-d]azepin-3-amine

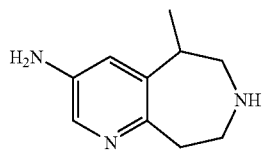

A mixture of 2-methoxy-5-methyl-3-nitro-7-(trifluoroacetyl)-6,7,8,9-tetrahydro-5H-pyrido[2,3-d]azepine (2.00 g, 6.00 mmol), HBr/AcOH (33 wt %, 20 ml) and H20 (5 ml) was stirred for 10 min at room temperature. The reaction was parted between sat. aq. NaHCO₃ and EtOAc. The organic phased was dried and concentrated in vacuo to give 1.68 g (88%) of pure 5-methyl-3-nitro-7-(trifluoroacetyl)-6,7,8,9-tetrahydro-5H-pyrido[2,3-d]azepin-2-ol. ¹H-NMR (CDCl₃) δ 8.42 (s, 1H), 4.20-3.20 (m, 8H), 1.45 (d, 1.2H), 1.39 (d, 1.8H) ppm. A mixture of 5-methyl-3-nitro-7-(trifluoroacetyl)-6,7,8,9-tetrahydro-5H-pyrido[2,3-d]azepin-2-ol (1.63 g, 5.10 mmol), Bu₄NBr (4.94 g, 15.3 mmol), P₂O₅ (3.62 g, 12.8 mmol) and toluene (100 ml) was heated to 110° C. for 5 h. The reaction was cooled to room temperature and the liquid part was decanted and concentrated in vacuo to give 1.25 g (64%) of pure 2-bromo-5-methyl-3-nitro-7-(trifluoroacetyl)-6,7,8,9-tetrahydro-5H-pyrido[2,3-d]azepine. ¹H-NMR (CDCl₃) δ 8.05 (s, 1H), 3.80 (m, 3H), 3.60-3.25 (m, 4H), 1.41 (d, 1.2H), 1.35 (d, 1.8H) ppm. Concurrent reduction of the nitro group and halogene on was carried out with 5% Pd/C in MeOH under H₂ (1 atm) to give 1.20 g (97%) of pure 5-methyl-7-(trifluoroacetyl)-6,7,8,9-tetrahydro-5H-pyrido[2,3-d]azepin-3-amine. ¹H-NMR of rotamers (MeOH-d₄) δ 7.77 (2× d, 1H), 7.62 (d, 0.4H), 7.58 (d, 0.6H), 4.10-3.35 (m, 7H), 1.42 (d, 1.3H), 1.35 (d, 1.7H) ppm. A mixture of 5-methyl-7-(trifluoroacetyl)-6,7,8,9-tetrahydro-5H-pyrido[2,3-d]azepin-3-amine (130 mg, 476 μmol), K₂CO₃ (100 mg), MeOH (6 ml) and H₂O (1 ml) was stirred for 16 h at room temprature. The reaction mixture was parted between aq. NaHCO₃ and DCM, the organic layer was dried and then concentrated in vacuo. The resulting residue was purified by column chromatography to yield 20.0 mg (24%) of 5-methyl-6,7,8,9-tetrahydro-5H-pyrido[2,3-d]azepin-3-amine. ¹H-NNMR (MeOH-d₄) δ 7.68 (s, 1H), 7.24 (s, 1H), 3.45-2.95 (m, 7H), 1.37 (d, 3H) ppm.

30) 3-Bromo-5-methyl-6,7,8,9-tetrahydro-5H-pyrido[2,3-d]azepine

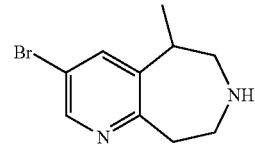

A mixture of 5-methyl-7-(trifluoroacetyl)-6,7,8,9-tetrahydro-5H-pyrido[2,3-d]azepin-3-amine (490 mg, 1.80 mmol), ᵗBuNO₂ (315 μl, 2.70 mmol), CuBr₂ (481 mg, 2.20 mmol) and MeCN (10 ml) was heated to 70° C. for 5 h. The reaction mixture was parted between H₂O and EtOAc, the organic layer was dried and then concentrated in vacuo. The resulting residue was purified by column chromatography to yield 100 mg (16%) of 3-bromo-5-methyl-7-(trifluoroacetyl)-6,7,8,9-tetrahydro-5H-pyrido[2,3-d]azepine. ¹H-NMR (CDCl₃) δ 8.46 (s, 1H), 7.64 (s, 1H), 4.25-3.20 (m, 7H), 1.39 (d, 1.3H), 1.35 (d, 1.65H) ppm. A mixture of 3-bromo-5-methyl-7-(trifluoroacetyl)-6,7,8,9-tetrahydro-5H-pyrido[2,3-d]azepine (90 mg, 267 μmol), K₂CO₃ (100 mg), MeOH (6 ml) and H₂O (1 ml) was stirred for 16 h at room temprature. The reaction mixture was parted between aq. NaHCO₃ and DCM, the organic layer was dried and then concentrated in vacuo. The resulting residue was purified by column chromatography to yield 25.0 mg (39%) of 3-bromo-5-methyl-6,7,8,9-tetrahydro-5H-pyrido[2,3-d]azepine. ¹H-NMR (MeOH-d₄) δ 8.49 (s, 1H), 7.90 (s, 1H), 3.55-3.40 (m, 3H), 3.37-3.27 (m, 2H), 3.20 (dd, 1H), 3.11 (dd, 1H), 1.48 (d, 3H) ppm.

Scheme II

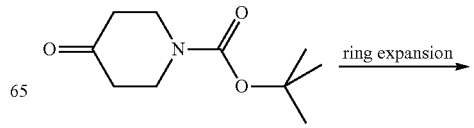

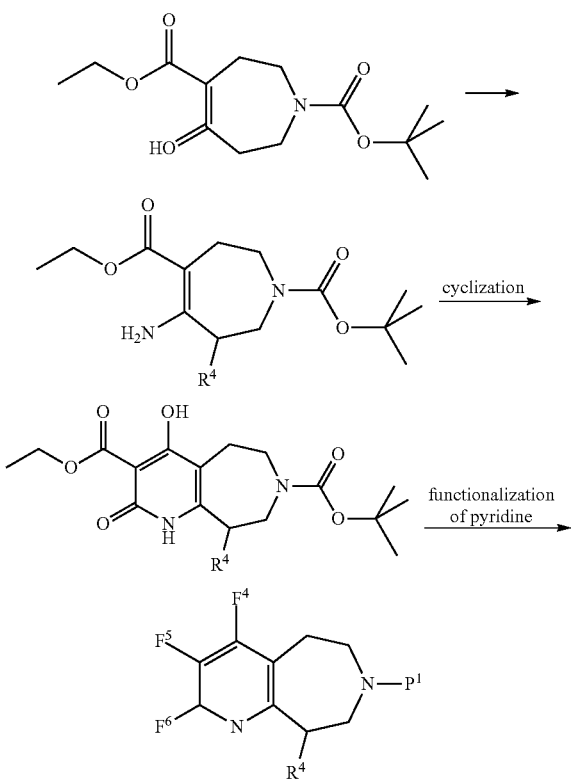

F4 = H, halogen
F5 = H, halogen, NO2, amino, alkylamino, dialkylamino
F6 = H, halogen, OH, amino, alkylamino, dialkylamino Synthesis of tert-butyl 4-hydroxy-2-oxo-1,2,5,6,8,9-hexahydro-7H-pyrido[2,3-d]azepine-7-carboxylate

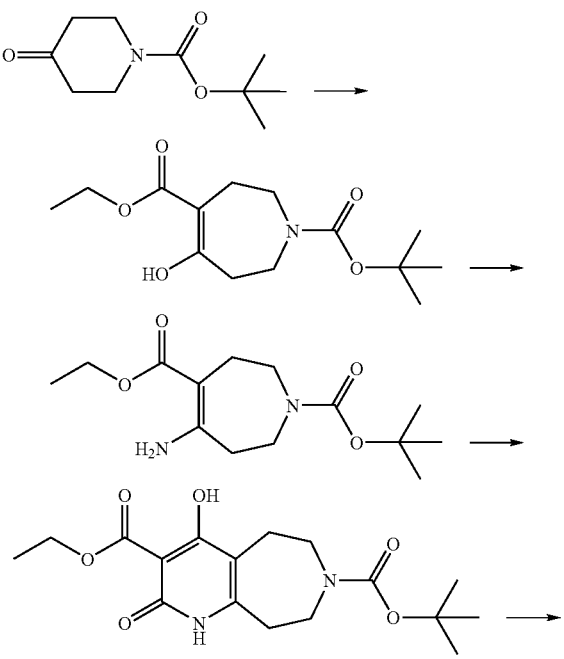

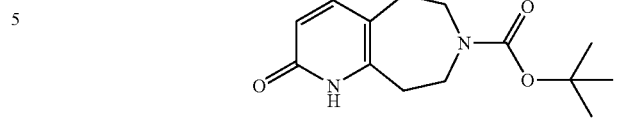

Ethyl diazoacetate (66.72 mmol, 6.93 ml) and BF$_3$Et$_2$O (56.45 mmol, 7.09 ml) were simultaneously, but independently added during several minutes to a stirred solution of 'butyl 4-oxopiperidine-1-carboxylate (51.32 mmol, 10.21 g) in anhydrous diethyl ether (50 ml) at −10° C. The mixture was stirred for an additional 3 hours while being allowed to warm to room temperature. Aqueous K$_2$CO$_3$ was added dropwise to the stirred mixture until gaseous evolution ceased. The reaction mixture was parted between ether and water. The organic layer was dried and concentrated in vacuo to afford 14.17 g (97%) of 1-tert-butyl 4-ethyl 5-hydroxy-2,3,6,7-tetrahydro-1H-azepine-1,4-dicarboxylate. A mixture of 1-tert-butyl 4-ethyl 5-hydroxy-2,3,6,7-tetrahydro-1H-azepine-1,4-dicarboxylate (17.61 mmol, 5.02 g), MeOH (45 ml) and NH$_4$OAc (176.1 mmol, 13.57 g) was stirred at room temperature until the starting material totally disappeared (~12 h). The reaction mixture was then concentrated under reduced pressure and re-dissolved in DCM. Extraction wit sat. aq. NaHCO$_3$ was followed by drying and concentration in vacuo to furnish 4.98 g (99%) of 1-tert-butyl 4-ethyl 5-amino-2,3,6,7-tetrahydro-1H-azepine-1,4-dicarboxylate. $^1$H-NMR (CDCl$_3$) δ 4.15 (2H), 3.55 (2H), 3.41 (2H), 2.59 (2H), 2.48 (2H), 1.46 (9H), 1.28 (3H) ppm. Ethyl malonyl chloride (7.76 mmol, 0.975 ml) was added dropwise over several minutes to a stirred solution of 1-tert-butyl 4-ethyl 5-amino-2,3,6,7-tetrahydro-1H-azepine-1,4-dicarboxylate (7.05 mmol, 2.00 g) and Et$_3$N (14.10 mmol, 1.97 ml) in DCM (34 ml) at 0° C. After 2 h of stirring, the suspension was concentrated under reduced pressure, diluted with EtOAc and successively washed with sat. aq. NaHCO$_3$, H$_2$O and brine. The organic layer was dried and concentrated to give a viscous oil. The crude material was dissolved in EtOH (35 ml) and then treated with NaOEt (21.16 mmol, 1.44 g) for 3 h at room temperature. EtOH was evaporated to give the sodium salt of the desired product which was washed several times with 20% EtOAc/hexanes. The crude sodium salt was diluted with water, acidified with 2 N HCl (pH 7) and extracted with EtOAc. The organic layer was dried and concentrated in vacuo to give 1.12 g (45%) of 7-tert-butyl 3-ethyl 4-hydroxy-2-oxo-1,2,5,6,8,9-hexahydro-7H-pyrido[2,3-d]azepine-3,7-dicarboxylate. $^1$H-NMR (CDCl$_3$) δ 13.97 (1H), 12.21 (1H), 4.46 (2H), 3.67 (2H), 3.57 (2H), 2.94 (2H), 2.84 (2H), 1.51 (9 H), 1.45 (3 H) ppm. 2 N NaOH (13 ml) was added to 7-tert-butyl 3-ethyl 4-hydroxy-2-oxo-1,2,5,6,8,9-hexahydro-7H-pyrido[2,3-d]azepine-3,7-dicarboxylate (0.95 g, 2.70 mmol) and the reaction mixture was heated to reflux for 3 h. After cooling to room temperature and acidifying to pH 0, the mixture was extracted with EtOAc. The organic layer was dried over Na$_2$SO$_4$ and concentrated under reduced pressure to give 757 mg (99%) of tert-butyl 4-hydroxy-2-oxo-1,2,5,6,8,9-hexahydro-7H-pyrido[2,3-d]azepine-7-carboxylate. $^1$H-NMR (DMSO-d$_6$) δ 10.81 (1H), 10.68 (1H), 5.50 (1H), 3.48 (2H), 3.39 (2H), 2.72 (2H), 2.60 (2H), 1.42 (9 H) ppm.

31) 3-Bromo-2-methoxy-6,7,8,9-tetrahydro-5H-pyrido[2,3-d]azepin-4-ol

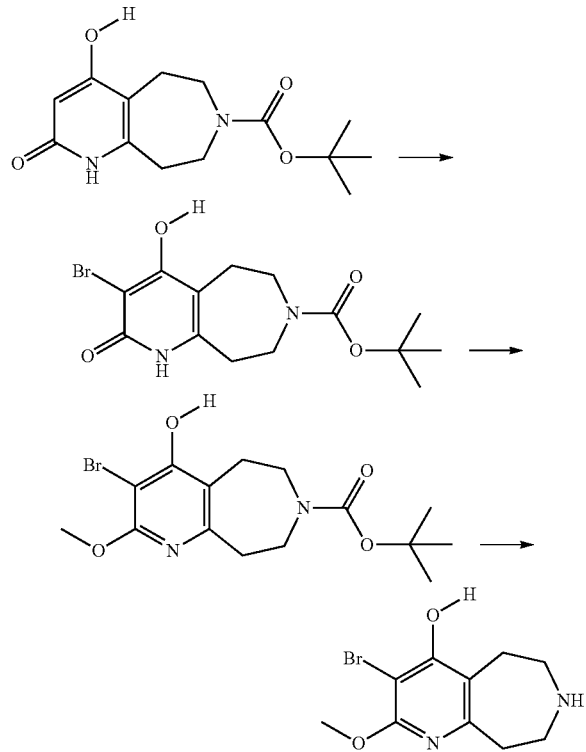

NBS (0.668 mmol, 119 mg) was added in one portion to a stirred solution of tert-butyl 4-hydroxy-2-oxo-1,2,5,6,8,9-hexahydro-7H-pyrido[2,3-d]azepine-7-carboxylate (0.607 mmol, 170 mg) in DCM (3 ml) at room temperature. After 3 h of stirring, the reaction was quenched with sat. aq. NaHCO$_3$ and extracted with DCM. The organic layer was dried, concentrated in vacuo and purified purified by column chromatography to provide 180 mg (83%) of tert-butyl 3-bromo-4-hydroxy-2-oxo-1,2,5,6,8,9-hexahydro-7H-pyrido[2,3-d]azepine-7-carboxylate. Ag$_2$CO$_3$ (0.42 mmol, 116 mg) was added to a solution of tert-butyl 3-bromo-4-hydroxy-2-oxo-1,2,5,6,8,9-hexahydro-7H-pyrido[2,3-d]azepine-7-carboxylate (75.0 mg, 0.21 mmol) in DCM (1.5 ml) at room temperature. After 10 min of stirring, MeI (0.23 mmol, 15 µl) was added. After 5 h of stirring, sat. aq. NH$_4$Cl was added and the mixture was extracted with DCM. The organic layer was washed with water, dried over Na$_2$SO$_4$ and concentrated under reduced pressure. The crude product was purified by column chromatography to provide 52 mg (67%) of tert-butyl 3-bromo-4-hydroxy-2-methoxy-5,6,8,9-tetrahydro-7H-pyrido[2,3-d]azepine-7-carboxylate. The correct regioselectivity was confirmed by NOESY. $^1$H-NMR (CDCl$_3$) δ 13.21 (1H), 3.85 (3H), 3.65 (2H), 3.55 (2H), 3.05 (2H), 2.85 (2H), 1.49 (9H) ppm. To a solution of tert-butyl 3-bromo-4-hydroxy-2-methoxy-5,6,8,9-tetrahydro-7H-pyrido[2,3-d]azepine-7-carboxylate (51 mg, 0.137 mmol) was added HCl (2 N in Et$_2$O, 3 ml) at room temperature. After 10 h of stirring, the reaction was quenched with sat. aq. NaHCO$_3$ and extracted with DCM. The organic layer was dried and concentrated in vacuo to provide 33 mg (89%) of 3-bromo-2-methoxy-6,7,8,9-tetrahydro-5H-pyrido[2,3-d]azepin-4-ol.

$^1$H-NMR (CDCl$_3$) δ 12.02 (br s, 1H), 9.21 (br s, 1H), 3.79 (3H), 3.25 (m, 2H), 3.15 (m, 2H), 3.06 (m, 2H), 2.92 (m, 2H) ppm.

32) 2,4-Dimethoxy-6,7,8,9-tetrahydro-5H-pyrido[2,3-d]azepine

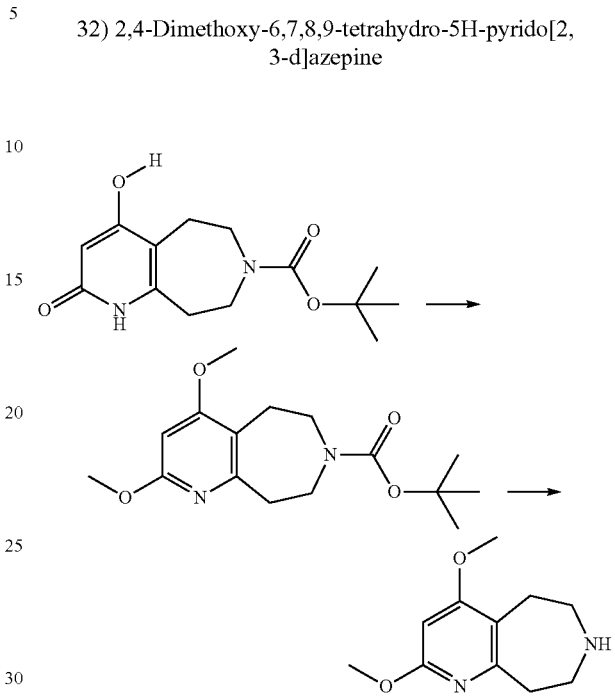

Ag$_2$CO$_3$ (1.63 mmol, 449 mg) was added to a solution of tert-butyl 4-hydroxy-2-oxo-1,2,5,6,8,9-hexahydro-7H-pyrido[2,3-d]azepine-7-carboxylate (91.0 mg, 0.325 mmol) in DCM (1.5 ml) at room temperature. After 10 min of stirring, MeI (1.63 mmol, 106 µl) was added. After 15 h of stirring, sat. aq. NH$_4$Cl was added and the mixture was extracted with DCM. The organic layer was washed with water, dried over Na$_2$SO$_4$ and concentrated under reduced pressure. The crude product was purified by column chromatography to provide 72 mg (72%) of tert-butyl 2,4-dimethoxy-5,6,8,9-tetrahydro-7H-pyrido[2,3-d]azepine-7-carboxylate. $^1$H-NMR (CDCl$_3$) δ 6.02 (1H), 3.85 (3H), 3.76 (3H), 3.55 (2H), 3.48 (2H), 2.98 (2H), 2.81 (2H), 1.45 (9H) ppm. tert-Butyl 2,4-dimethoxy-5,6,8,9-tetrahydro-7H-pyrido[2,3-d]azepine-7-carboxylate (72 mg, 0.23 mmol) was dissolved in HCl (2 N in Et$_2$O, 3 ml) and stirred for 16 h at room temperature. The hydrochloric salt of 2,4-dimethoxy-6,7,8,9-tetrahydro-5H-pyrido[2,3-d]azepine was obtained in quantitative yield. $^1$H-NMR (CDCl$_3$) δ 9.98 (br s, 2H), 6.32 (s, 1H), 3.73 (s, 3H), 3.65 (s, 3H), 3.25 (m, 2H), 2.88 (m, 2H), 2.86 (m, 2H), 2.78 (m, 2H) ppm.

33) 2-Methoxy-6,7,8,9-tetrahydro-5H-pyrido[2,3-d]azepin-4-ol

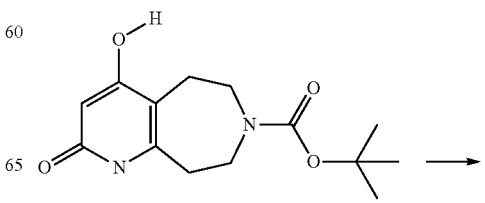

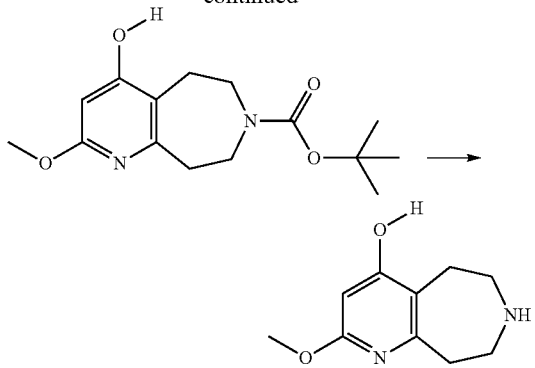

Selective methylation with MeI and Ag₂CO₃ was achieved as descibed above for 31). ¹H-NMR (DMSO-d₆) δ 10.98 (1H), 5.62 (1H), 3.74 (3H), 3.48 (2H), 3.38 (2H), 2.76 (2H), 2.62 (2H), 1.39 (9H) ppm. N-deprotection was achieved as described above for 31) ¹H-NMR (DMSO-d₆) δ 6 9.46 (br s, 1H), 6.01 (s, 1H), 3.81-3.08 (m, 6H), 2.92 (m, 2H) ppm.

34) Ethyl 2,4-dimethoxy-6,7,8,9-tetrahydro-5H-pyrido[2,3-d]azepine-3-carboxylate

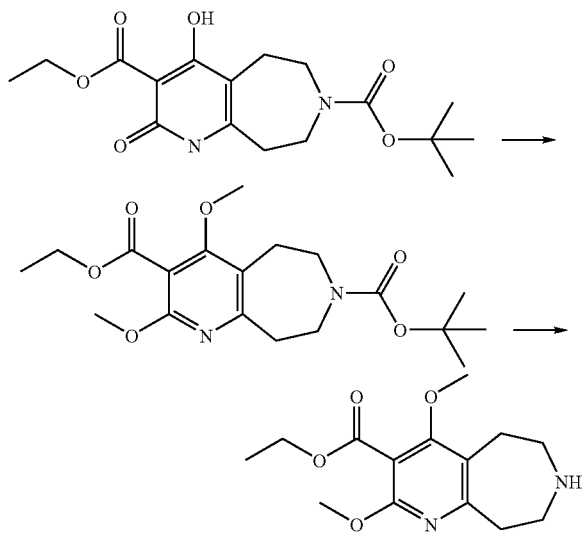

Methylation with MeI and Ag₂CO₃ was achieved as descibed above for 32). ¹H-NMR (CDCl₃) δ 4.41 (2H), 3.90 (3H), 3.86 (3H), 3.64 (4H), 3.14 (2H), 2.84 (2H), 1.55 (9H), 1.41 (3 H) ppm. N-deprotection was achieved as described above for 32). ¹H-NMR (CDCl₃) δ 4.41 (q, 2H), 3.98 (s, 3H), 3.80 (s, 3H), 3.08 (m, 2H), 2.99 (m, 2H), 2.94 (m, 2H), 2.88 (m, 2H), 2.15 (br s, 1.7H), 1.40 (t, 3 H) ppm.

Synthesis of tert-butyl 4-hydroxy-9-methyl-2-oxo-1,2,5,6,8,9-hexahydro-7H-pyrido[2,3-d]azepine-7-carboxylate

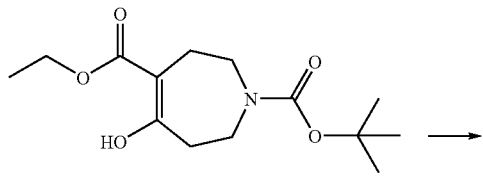

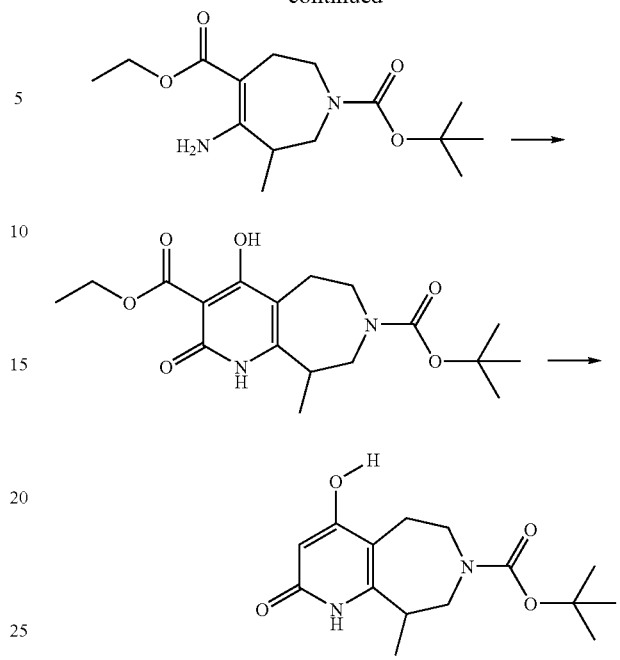

A solution of 1-tert-butyl 4-ethyl 5-hydroxy-2,3,6,7-tetrahydro-1H-azepine-1,4-dicarboxylate (14.11 mmol, 4.02 g) in anhydrous THF (15 ml) was added to a stirred solution of freshly prepared iPr₂NLi (43.74 mmol) in anhydrous THF (95 ml) at –78° C. The reaction mixture was stirred at –78° C. for 1 h and HMPA (42.33 mmol, 7.38 ml) was added followed by MeI (14.11 mmol, 0.97 ml). The reaction mixture was slowly warmed to room temperature and stirred overnight before being quenched with sat. aq. NH₄Cl. After addition of water, the reaction mixture was extracted with EtOAc. The organic layer was washed with brine, dried over Na₂SO₄ and concentrated under reduced pressure. The crude mixture was treated with NH₄OAc and MeOH in the same manner described above and furnished 1-tert-butyl 4-ethyl 5-amino-6-methyl-2,3,6,7-tetrahydro-1H-azepine-1,4-dicarboxylate in 76% yield. MS (ESI) m/z 299 [M+1]⁺7-tert-Butyl 3-ethyl 4-hydroxy-9-methyl-2-oxo-1,2,5,6,8,9-hexahydro-7H-pyrido[2,3-d]azepine-3,7-dicarboxylate was obtained in comparable yields from 1-tert-butyl 4-ethyl 5-amino-6-methyl-2,3,6,7-tetrahydro-1H-azepine-1,4-dicarboxylate applying the cyclization procedure described for the synthesis of tert-butyl 4-hydroxy-2-oxo-1,2,5,6,8,9-hexahydro-7H-pyrido[2,3-d]azepine-7-carboxylate. ¹H-NMR (CDCl₃) δ 13.97 (1H), 11.54 (1H), 4.47 (2H), 3.94 (1H), 3.82 (1H), 3.41 (1H), 3.15 (3H), 2.61 (1 H), 1.46 (9 H), 1.42 (3H), 1.31 (3H) ppm. tert-Butyl 4-hydroxy-9-methyl-2-oxo-1,2,5,6,8,9-hexahydro-7H-pyrido[2,3-d]azepine-7-carboxylate was obtained in comparable yields from 7-tert-butyl 3-ethyl 4-hydroxy-9-methyl-2-oxo-1,2,5,6,8,9-hexahydro-7H-pyrido[2,3-d]azepine-3,7-dicarboxylate applying the decarboxylation procedure described for the synthesis of tert-butyl 4-hydroxy-2-oxo-1,2,5,6,8,9-hexahydro-7H-pyrido[2,3-d]azepine-7-carboxylate. ¹H-NMR (DMSO-d₆) δ 10.75 (2H), 5.50 (1H), 3.61 (2H), 3.51 (1H), 3.06 (2H), 2.91 (1H), 2.48 (1H), 1.39 (9 H), 1.12 (3 H) ppm.

35) 2-Bromo-9-methyl-6,7,8,9-tetrahydro-5H-pyrido[2,3-d]azepine

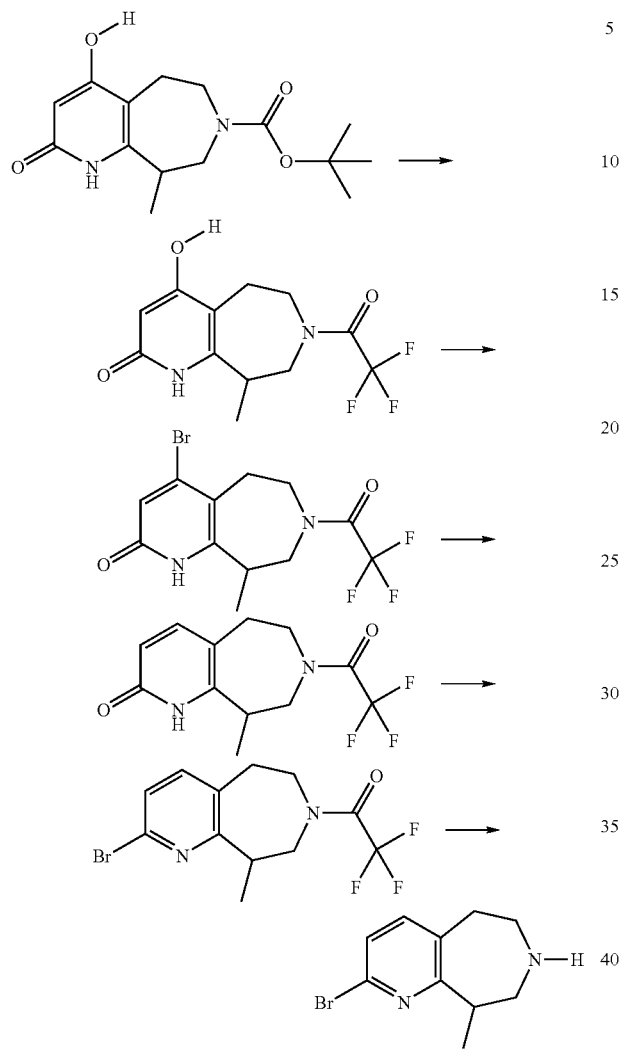

TFA (9.20 mmol, 0.709 ml) was slowly added to a stirred solution of tert-butyl 4-hydroxy-9-methyl-2-oxo-1,2,5,6,8,9-hexahydro-7H-pyrido[2,3-d]azepine-7-carboxylate (0.541 g, 1.84 mmol) in DCM (20 ml) at room temperature. The reaction solution was stirred until all starting materials are consumed. The solvent was removed under reduced pressure and the resulting residue was dissolved in DCM (20 ml). Addition of Et$_3$N (18.4 mmol, 2.56 ml) and TFAA (3.86 mmol, 0.511 ml) was followed by stirring for 8 h at room temperature. The reaction mixture was parted between sat. aq. NaHCO$_3$ and DCM. The organic layer was dried over Na$_2$SO$_4$, concentrated under reduced pressure and purified to provide 277 mg (52%, two steps) of 4-hydroxy-9-methyl-7-(trifluoroacetyl)-1,5,6,7,8,9-hexahydro-2H-pyrido[2,3-d]azepin-2-one. MS (ESI) m/z 291 [M+1]$^+$. POBr$_3$ (0.533 mol, 153 mg) was added to a stirred solution of 4-hydroxy-9-methyl-7-(trifluoroacetyl)-1,5,6,7,8,9-hexahydro-2H-pyrido[2,3-d]azepin-2-one (77 mg, 266 µmol) in DMF (1 ml). The mixture was heated at 90° C. for 2 h, quenched with sat. aq. NaHCO$_3$ and extracted with EtOAc. The organic layer was dried over Na$_2$SO$_4$, concentrated under reduced pressure and purified by column chromatography to furnish 47 mg (50%) of 4-bromo-9-methyl-7-(trifluoroacetyl)-1,5,6,7,8,9-hexahydro-2H-pyrido[2,3-d]azepin-2-one. MS (ESI) m/z 353/355. A mixture of 4-bromo-9-methyl-7-(trifluoroacetyl)-1,5,6,7,8,9-hexahydro-2H-pyrido[2,3-d]azepin-2-one (47 mg, 134 µmol), EtOH (2 ml) and 10% Pd/C was stirred for 5 minutes under H2 atmosphere (1 atm). The reaction was filtered through Celite and 35 mg (99%) of 9-methyl-7-(trifluoroacetyl)-1,5,6,7,8,9-hexahydro-2H-pyrido[2,3-d]azepin-2-one was obtained. MS (ESI) m/z 275. POBr$_3$ (256 µmol, 73.5 mg) was added to a stirred solution of 9-methyl-7-(trifluoroacetyl)-1,5,6,7,8,9-hexahydro-2H-pyrido[2,3-d]azepin-2-one (35 mg, 128 µmol) in DMF (1 ml). The mixture was heated at 90° C. for 5 h, quenched with sat. aq. NaHCO$_3$ and extracted with EtOAc. The organic layer was dried over Na$_2$SO$_4$, concentrated under reduced pressure and purified by column chromatography to furnish 24 mg (56%) of 2-bromo-9-methyl-7-(trifluoroacetyl)-6,7,8,9-tetrahydro-5H-pyrido[2,3-d]azepine. MS (ESI) m/z 337/339. Deprotection was carried out at 60° C. for 10 minutes using MeOH (1 ml), H$_2$O (200 µl) and K$_2$CO$_3$ (30 mg) to render 15 mg (87%) of 2-bromo-9-methyl-6,7,8,9-tetrahydro-5H-pyrido[2,3-d]azepine. $^1$H-NMR (DMSO-d$_6$) δ 7.42 (d, 1H), 7.35 (d, 1H), 4.25 (m, 2H), 3.86 (m, 2H), 3.18 (m, 2H), 2.84 (dd, 1H), 1.21 (d, 3H) ppm.

36) 9-Methyl-6,7,8,9-tetrahydro-5H-pyrido[2,3-d]azepine-2,4-diol

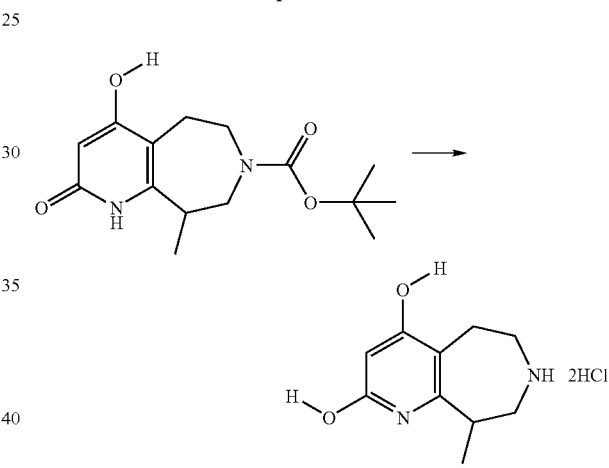

HCl (2 N in Et$_2$O, 5 ml) was added dropwise to a stirred solution of tert-butyl 4-hydroxy-9-methyl-2-oxo-1,2,5,6,8,9-hexahydro-7H-pyrido[2,3-d]azepine-7-carboxylate (250 mg, 850 µmol). After 10 h of stirring at room temperature, the reaction was quenched with sat. aq. NaHCO$_3$ and extracted with DCM. The organic layer was dried and concentrated in vacuo to provide 180 mg (92%) of 4-hydroxy-9-methyl-1,5,6,7,8,9-hexahydro-2H-pyrido[2,3-d]azepin-2-one. $^1$H-NMR (DMSO-d$_6$) δ 13.20 (br s, 2H), 12.93 (br s, 2H), 10.02 (br s, 1H), 9.41 (br s, 1H), 6.65 (s, 1H), 3.51 (br s, 1H), 3.32 (m, 2H), 3.15 (m, 2H), 2.95 (m, 1 H), 2.85 (m, 1 H), 1.39 (d, 3H) ppm.

37) 3,4-Dibromo-2-methoxy-5,7-dimethyl-6,7,8,9-tetrahydro-5H-pyrido[2,3-d]azepine

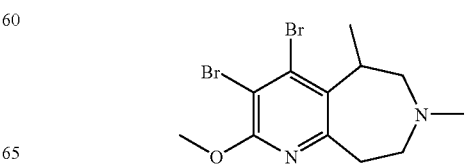

A mixture of 3,4-dibromo-2-methoxy-5-methyl-6,7,8,9-tetrahydro-5H-pyrido[2,3-d]azepine (32.5 mg, 9.30 µmol), MeI (5.8 µl, 93.0 µmol), Na$_2$CO$_3$ (19.7 mg, 18.3 µmol) and DMF (5 ml) was stirred for 3 d at room temperature. The reaction was quenched with sat. aq. NaHCO$_3$ and extracted with EtOAc. The organic layer was dried over Na$_2$SO$_4$, concentrated in vacuo and purified by column chromatography to give 19.0 mg (56%) of 3,4-dibromo-2-methoxy-5,7-dimethyl-6,7,8,9-tetrahydro-5H-pyrido[2,3-d]azepine. $^1$H-NMR (CDCl$_3$) δ 3.89 (s, 3H), 3.63 (m, 1H), 3.25 (m, 1H), 2.88 (m, 3H), 2.30 (s, 3H), 2.28 (dd, 1H), 2.14 (m, 1H), 1.26 (d, 3H) ppm.

The separation of racemic 6,7,8,9-tetrahydro-5H-pyrido[2,3-d]azepines into their respective enantiomers was carried out on selected compounds by chiral HPLC utilizing a Waters HPLC Daicel Chiralcel OD-H (5µ 20 mm×250 mm) column. The mobile phase consisted of 0.1% TFA in EOH and hexanes (6:94 v:v). Compounds were diluted and injected (25-100 µl) with iPrOH. The run time was 20 minutes (7.5 ml/min) and the enantiomers eluted between 10-16 minutes.

The resolution of racemic 6,7,8,9-tetrahydro-5H-pyrido[2,3-d]azepines into their respective enantiomers was also carried out on selected compounds by co-crystallization with (+)- or (−)-O,O'-dibenzoyl-D-tartaric acid in MeOH. The optical purity was determined using reversed phase HPLC by means of the corresponding Mosher amide which was formed by reacting the free base of the precipitated (R)- or (S)-5-methyl-6,7,8,9-tetrahydro-5H-pyrido[2,3-d]azepine with (R)-(−)- or (S)-(+)-α-methoxy-α-(trifluoromethyl)phenylacetyl chloride. The optical purity was also determined by chiral HPLC utilizing a Waters HPLC Daicel Chiralcel OD-H (5µ 20 mm×250 mm) column. The mobile phase consisted of 0.1% TFA in EOH and hexanes (6:94 v:v). Compounds were diluted and injected (25-100 µl) with iPrOH. The run time was 20 minutes (7.5 ml/min) and the enantiomers eluted between 10-16 minutes.

Using the procedures described above, the following compounds were prepared.

3-Bromo-2-methoxy-5-methyl-6,7,8,9-tetrahydro-5H-pyrido[2,3-d]azepine (Example 5) afforded (5R)- and (5S)-3-bromo-2-methoxy-5-methyl-6,7,8,9-tetrahydro-5H-pyrido[2,3-d] azepine.

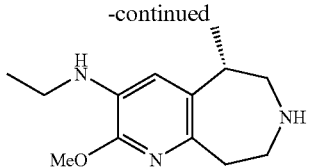

4-Chloro-N-ethyl-2-methoxy-5-methyl-6,7,8,9-tetrahydro-5H-pyrido[2,3-d]azepin-3-amine (Example 25) afforded (5R)- and (5S)-4-chloro-N-ethyl-2-methoxy-5-methyl-6,7,8,9-tetrahydro-5H-pyrido[2,3-d]azepin-3-amine.

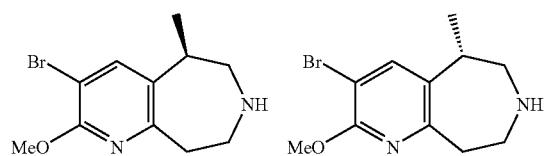

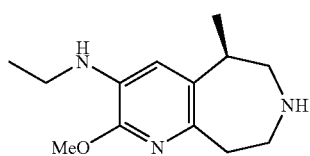

3-Bromo-4-chloro-2-methoxy-5-methyl-6,7,8,9-tetrahydro-5H-pyrido[2,3-d]azepine (Example 27) afforded (5R)- and (5S)-3-bromo-4-chloro-2-methoxy-5-methyl-6,7,8,9-tetrahydro-5H-pyrido[2,3-d]azepine.

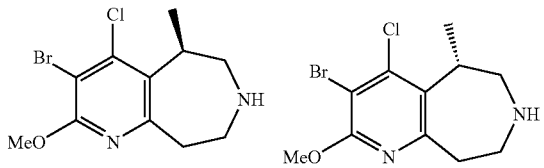

In-vitro Radioligand Binding Assay for Evaluation of the Agonist Affinity for the Human Serotonin 5-HT$_{2C}$ Receptor in Transfected CHO Cells Cell membrane homogenates (40 µg protein) were incubated for 15 min at 37° C. with 0.2 nM [$^{125}$I]DOI in the presence of the test compound in a buffer containing 50 mM Tris-HCl (pH 7.4), 5 mM MgCl$_2$ and 0.3% BSA. Nonspecific binding was determined in the presence of 10 µM DOI. Following incubation, the samples were filtered rapidly under vacuum through glass fiber filters presoaked with 0.3% PEI and rinsed several times with 0° C. cold 50 mM Tris-HCl using a 96-sample cell harvester. The filters were dried then counted for radioactivity in a scintillation counter using a scintillation cocktail (Microscint 0, Packard). The results were expressed as a percent inhibition of the control radioligand specific binding. The standard reference compound was DOI.

Fluorometric Functional Assay for Evaluation of the Agonist Activity for Human Serotonin 5-HT$_{2C}$ Receptor-Mediated Ca$^{2+}$ Mobilization in Human Recombinant Cells (CHO)

CHO cells (2×10$^4$ cells/well) were incubated for 90 min at 37° C. in a HBSS buffer (pH 7.4) containing 20 mM Hepes/NaOH, 138 mM NaCl, 5.33 mM KCl, 1.25 mM CaCl$_2$, 0.5 mM MgCl$_2$, 0.41 mM MgSO$_4$, 0.3 mM Na$_2$HPO$_4$, 0.441 mM KH$_2$PO$_4$, 0.1% glucose, 2.5 mM Probenecid (MDR inhibitor) and a fluorescent probe. The test compound was injected by a CellLux reader (Perkin Elmer). The kinetic of the changes in cytosolic Ca$^{2+}$ is then measured by the CellLux reader. The fluorescence intensity, proportional to the Ca$^{2+}$ mobilization, is expressed in arbitrary unit of fluorescence. Specificity of the changes is controlled in parallel with 5-HT at 1 µM. The results are expressed as a percent stimulation relative to serotonin control activity. The standard reference agonist is 5-HT.

Inhibition of Food Intake in Food-Deprived Rats

Selected compounds were evaluated for their effect in the inhibition of food intake in food-deprived Sprague Dowley male rats. The animals were individually caged under pathogen-free conditions and allowed to acclimatize for 7 days while being fed fresh rodent chow. Then, the animals were fasted overnight, weighed, and randomized in the experimental grouping to 8 animals per group, according to body weights. All shavings were removed from the cages and the animals were dosed p.o. with the vehicle, a positive control and the test compounds. The administered doses were calculated to be about 100 µmol/kg. After one hour dosing, the animals were presented with a pre-weighted amount of rodent chow in a petri dish. The amount of food left after 1, 2, 4, and 6 hours post food presentation was recorded. Compounds tested in this experiment exhibited an inhibitory effect of 40% to 90% after 1 h and 25% to 45% after 6 h, respectively.

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:
1. A compound of formula I:

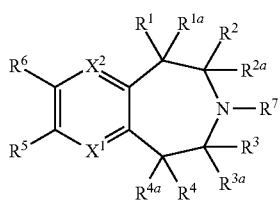

(I)

wherein
$R^1$, $R^{1a}$, $R^4$ and $R^{4a}$ are each independently hydrogen, hydroxyl, alkyl, alkenyl, aryl, alkoxy, aryloxy, amino, alkylamino or arylamino;
$R^2$, $R^{2a}$, $R^3$ and $R^{3a}$ are each independently hydrogen or alkyl;
or $R^1$ and $R^{1a}$ or $R^2$ and $R^{2a}$ or $R^3$ and $R^{3a}$ or $R^4$ and $R^{4a}$, together with the carbon atom to which they are attached, independently form a C=O or C=CRR' group where R and R' are independently hydrogen or alkyl;
$R^5$ and $R^6$ are each independently hydrogen, halogen, hydroxyl, alkyl, alkenyl, aryl, arylalkyl, alkoxy, alkenyloxy, aryloxy, nitro, amino, alkylamino, dialkylamino, arylamino, diarylamino or —C(O)OR$^8$ in which R$^8$ is hydrogen, alkyl or aryl;
$R^7$ is hydrogen, —C(O)R$^9$, —C(O)OR$^9$, C(O)NR$^9$R$^{10}$, —S(O)$_2$R$^{11}$ or —S(O)R$^{11}$, in which R$^9$ and R$^{10}$ are each independently hydrogen, halogen, alkyl or aryl and R$^{11}$ is alkyl or aryl;
$X^1$ and $X^2$ are independently N, or CR$^{12}$ in which R$^{12}$ is hydrogen, halogen, hydroxyl, alkoxy, alkyl, or alkenyl, with the proviso that when $X^1$ is N, then $X^2$ is CR$^{12}$ and when $X^2$ is N, then $X^1$ is CR$^{12}$,
and pharmaceutically acceptable salts thereof;
with the proviso that said compound is not:
6,7,8,9-tetrahydro-2,3-diphenyl-5H-Pyrido[2,3-d] azepine,
2-amino-5,6,8,9-tetrahydro-7H-Pyrido [2,3-d]azepine-7-carboxylic acid 1,1-dimethylethyl ester,
6,7,8,9-tetrahydro-5H-Pyrido[2,3-d]azepin-2-amine,
5,6,8,9-tetrahydro-7H-Pyrido[2,3-d]azepine-3,7-dicarboxylic acid diethyl ester,
1,2,5,6,8,9-hexahydro-2-oxo-7H-Pyrido[2,3-d]azepine-7-carboxylic acid ethyl ester,
1,2,5,6,8,9-hexahydro-2-oxo-7H-Pyrido[2,3-d]azepine-3,7-dicarboxylic acid diethyl ester,
4-chloro-1,2,5,6,8,9-hexahydro-2-oxo-7H-Pyrido[2,3-d] azepine-7-carboxylic acid ethyl ester,
4-chloro-1,2,5,6,8,9-hexahydro-2-oxo-7H-Pyrido[2,3-d] azepine-3,7-dicarboxylic acid diethyl ester,
2,4-dichloro-5,6,8,9-tetrahydro-7H-Pyrido[2,3-d] azepine-3,7-dicarboxylic acid diethyl ester,
1,2,5,6,8,9-hexahydro-4-hydroxy-2-oxo-7H-Pyrido[2,3-d]azepine-7-carboxylic acid ethyl ester, or
1,2,5,6,8,9-hexahydro-4-hydroxy-2-oxo-7H-Pyrido[2,3-d]azepine-3,7-dicarboxylic acid diethyl ester.

2. A compound according to claim 1, wherein
$R^1$, $R^{1a}$, $R^4$ and $R^{4a}$ are each independently hydrogen, hydroxyl, alkyl, alkenyl, aryl, alkoxy, aryloxy, amino, alkylamino or arylamino;
$R^2$, $R^{2a}$, $R^3$ and $R^{3a}$ are each independently hydrogen or alkyl;
or $R^1$ and $R^{1a}$ or $R^2$ and $R^{2a}$ or $R^3$ and $R^{3a}$ or $R^4$ and $R^{4a}$, together with the carbon atom to which they are attached, independently form a C=O;
$R^5$ and $R^6$ are each independently hydrogen, halogen, hydroxyl, alkyl, alkenyl, aryl, alkoxy, alkenyloxy, aryloxy, nitro, amino, alkylamino, dialkylamino, arylamino or diarylamino;
$R^7$ is hydrogen, —C(O)OR$^9$, —C(O)NR$^9$R$^{10}$ or —S(O)$_2$R$^{11}$ in which R$^9$ and R$^{10}$ are each independently hydrogen, halogen, alkyl, or aryl and R$^{11}$ is alkyl or aryl; and
$X^1$ and $X^2$ are independently N, or CR$^{12}$ in which R$^{12}$ is hydrogen, halogen, hydroxyl, alkyl, or alkenyl, with the proviso that when $X^1$ is N, then $X^2$ is CR$^{12}$ and when $X^2$ is N, then $X^1$ is CR$^{12}$.

3. A compound according to claim 1, wherein
$R^1$, $R^{1a}$, $R^4$ and $R^{4a}$ are each independently hydrogen or alkyl;
$R^2$, $R^{2a}$, $R^3$ and $R^{3a}$ are each hydrogen;
or $R^1$ and $R^{1a}$ or $R^2$ and $R^{2a}$ or $R^3$ and $R^{3a}$ or $R^4$ and $R^{4a}$, together with the carbon atom to which they are attached, independently form a C=CRR' group where R and R' are hydrogen;
$R^5$ and $R^6$ are each independently hydrogen, halogen, hydroxyl, alkyl, alkenyl, alkoxy, alkenyloxy, nitro, amino, alkylamino, dialkylamino or —C(O)OR$^8$ in which R$^8$ is alkyl;
$R^7$ is hydrogen, —C(O)R$^9$ or —C(O)OR$^9$, in which R$^9$ is alkyl; and
$X^1$ and $X^2$ are independently N, or CR$^{12}$ in which R$^{12}$ is hydrogen, halogen, hydroxyl, alkoxy or alkyl, with the proviso that when $X^1$ is N, then $X^2$ is CR$^{12}$ and when $X^2$ is N, then $X^1$ is CR$^{12}$.

4. A compound according to claim 1, wherein at least one of $R^1$, $R^{1a}$, $R^2$, $R^{2a}$, $R^3$, $R^{3a}$, $R^4$ and $R^{4a}$ is other than hydrogen.

5. A compound according to claim 4, wherein $R^1$ is methyl and $R^{1a}$, $R^2$, $R^{2a}$, $R^3$, $R^{3a}$, $R^4$ and $R^{4a}$ are hydrogen.

6. A compound according to claim 4, wherein $R^1$ and $R^3$ are methyl and $R^{1a}$, $R^2$, $R^{2a}$, $R^{3a}$, $R^4$ and $R^{4a}$ are hydrogen.

7. A compound according to claim 4, wherein $R^4$ is methyl and $R^1$, $R^{1a}$, $R^2$, $R^{2a}$, $R^3$, $R^{3a}$ and $R^{4a}$ are hydrogen.

8. A compound according to claim 1, wherein $R^5$ and $R^6$ are each independently hydrogen, halogen, hydroxyl, alkyl, alkenyl, alkoxy, alkenyloxy, nitro, amino, alkylamino, dialkylamino or —C(O)OR$^8$.

9. A compound according to claim 1, wherein $R^5$ is hydrogen, halogen, hydroxyl, alkoxy, alkenyloxy or alkylamino.

10. A compound according to claim 1, wherein $R^6$ is hydrogen, halogen, alkyl, alkenyl, nitro, amino, alkylamino, dialkylamino or —C(O)OR$^8$.

11. A compound according to claim 1, wherein $R^5$ is hydroxyl, alkoxy or alkenyloxy and $R^6$ is hydrogen, halogen, alkenyl, alkyl, nitro, amino, alkylamino, dialkylamino or —C(O)OR$^8$.

12. A compound according to claim 1, wherein $R^7$ is hydrogen, —C(O)R$^9$ or —C(O)OR$^9$, in which R$^9$ is independently hydrogen or alkyl.

13. A compound according to claim 1, wherein $R^7$ is hydrogen, —C(O)-alkyl or —C(O)O-alkyl.

14. A compound according to claim 1, wherein $R^7$ is hydrogen or —C(O)OR$^9$.

15. A compound according to claim 1, wherein $X^1$ is N and $X^2$ is CR$^{12}$.

16. A compound according to claim 15, wherein $R^{12}$ is hydrogen, halogen, alkyl, hydroxyl or alkoxy.

17. A compound according to claim 1, wherein when $R^1$, $R^{1a}$, $R^2$, $R^{2a}$, $R^3$, $R^{3a}$, $R^4$ and $R^{4a}$ are hydrogen, then at least one of $R^5$ and $R^6$ is hydroxyl, alkoxy or alkenyloxy.

18. A compound according to claim 1, wherein $X^1$ is N, $X^2$ is CR$^{12}$ and $R^5$, $R^6$ and $R^{12}$ are other than H.

19. A compound according to claim 18, wherein $X^1$ is N, $X^2$ is CR$^{12}$ where $R^{12}$ is halogen, hydroxyl or alkoxy, and $R^5$ and $R^6$ are independently halogen, alkoxy, amino, alkylamino, dialkylamino or —C(O)OR$^8$.

20. A compound according to claim 1, wherein one of $R^1$, $R^{1a}$, $R^2$, $R^{2a}$, $R^3$, $R^{3a}$, $R^4$ and $R^{4a}$ is other than hydrogen, $X^1$ is N, $X^2$ is CR$^{12}$ where $R^{12}$ is hydrogen or halogen, $R^5$ is alkoxy and $R^6$ is halogen or alkylamino.

21. A compound according to claim 20, wherein $R^1$ is alkyl and $R^{1a}$, $R^2$, $R^{2a}$, $R^3$, $R^{3a}$, $R^4$ and $R^{4a}$ are hydrogen.

22. A compound according to claim 1, selected from:
3-bromo-2-methoxy-5,8-dimethyl-6,7,8,9-tetrahydro-5H-pyrido[2,3-d]azepine,
2-methoxy-5-methylene-6,7,8,9-tetrahydro-5H-pyrido[2,3-d]azepine,
2-methoxy-5-methyl-6,7,8,9-tetrahydro-5H-pyrido[2,3-d]azepine,
5-methyl-6,7,8,9-tetrahydro-5H-pyrido[2,3-d]azepin-2-ol,
3-bromo-2-methoxy-5-methyl-6,7,8,9-tetrahydro-5H-pyrido[2,3-d]azepine,
3-chloro-2-methoxy-5-methyl-6,7,8,9-tetrahydro-5H-pyrido[2,3-d]azepine,
3-bromo-5-methyl-6,7,8,9-tetrahydro-5H-pyrido[2,3-d]azepin-2-ol,
3-iodo-5-methyl-6,7,8,9-tetrahydro-5H-pyrido[2,3-d]azepin-2-ol,
2-chloro-3-iodo-5-methyl-6,7,8,9-tetrahydro-5H-pyrido[2,3-d]azepine,
3-iodo-2-methoxy-5-methyl-6,7,8,9-tetrahydro-5H-pyrido[2,3-d]azepine,
2-(allyloxy)-3-iodo-5-methyl-6,7,8,9-tetrahydro-5H-pyrido[2,3-d]azepine,
2-chloro-5-methyl-6,7,8,9-tetrahydro-5H-pyrido[2,3-d]azepine,
3-bromo-2-chloro-5-methyl-6,7,8,9-tetrahydro-5H-pyrido[2,3-d]azepine,
2-methoxy-5-methyl-3-vinyl-6,7,8,9-tetrahydro-5H-pyrido[2,3-d]azepine,
3-ethyl-2-methoxy-5-methyl-6,7,8,9-tetrahydro-5H-pyrido[2,3-d]azepine,
2-(difluoromethoxy)-5-methyl-6,7,8,9-tetrahydro-5H-pyrido[2,3-d]azepine,
3-bromo-N,5-dimethyl-6,7,8,9-tetrahydro-5H-pyrido[2,3-d]azepin-2-amine,
2-methoxy-5-methyl-3-nitro-6,7,8,9-tetrahydro-5H-pyrido[2,3-d]azepine,
2-methoxy-5-methyl-6,7,8,9-tetrahydro-5H-pyrido[2,3-d]azepin-3-amine,
2-methoxy-N,N,5-trimethyl-6,7,8,9-tetrahydro-5H-pyrido[2,3-d]azepin-3-amine,
4-bromo-2-methoxy-5-methyl-6,7,8,9-tetrahydro-5H-pyrido[2,3-d]azepin-3-amine,
N-ethyl-2-methoxy-5-methyl-6,7,8,9-tetrahydro-5H-pyrido[2,3-d]azepin-3-amine,
4-chloro-N-ethyl-2-methoxy-5-methyl-6,7,8,9-tetrahydro-5H-pyrido[2,3-d]azepin-3-amine,
3,4-dibromo-2-methoxy-5-methyl-6,7,8,9-tetrahydro-5H-pyrido[2,3-d]azepine,
3-bromo-4-chloro-2-methoxy-5-methyl-6,7,8,9-tetrahydro-5H-pyrido[2,3-d]azepine,
3,4-dichloro-2-methoxy-5-methyl-6,7,8,9-tetrahydro-5H-pyrido[2,3-d]azepine,
5-methyl-6,7,8,9-tetrahydro-5H-pyrido[2,3-d]azepin-3-amine,
3-bromo-5-methyl-6,7,8,9-tetrahydro-5H-pyrido[2,3-d]azepine,
3-bromo-2-methoxy-6,7,8,9-tetrahydro-5H-pyrido[2,3-d]azepin-4-ol,
2,4-dimethoxy-6,7,8,9-tetrahydro-5H-pyrido[2,3-d]azepine,
2-methoxy-6,7,8,9-tetrahydro-5H-pyrido[2,3-d]azepin-4-ol,
2,4-dimethoxy-6,7,8,9-tetrahydro-5H-pyrido[2,3-d]azepine-3-carboxylic acid ethyl ester,
2-bromo-9-methyl-6,7,8,9-tetrahydro-5H-pyrido[2,3-d]azepine,
9-methyl-6,7,8,9-tetrahydro-5H-pyrido[2,3-d]azepine-2,4-diol,
and pharmaceutically acceptable salts thereof,
wherein if the compound exhibits chirality it can be in the form of a mixture of enantiomers or a mixture of diastereomers, or can be in the form of a single enantiomer or a single diastereomer.

23. A compound according to claim 1, selected from:
(5R)-3-bromo-2-methoxy-5 -methyl-6,7,8,9-tetrahydro-5H-pyrido[2,3-d]azepine,
(5S)-3 -bromo-2-methoxy-5 -methyl-6,7,8,9-tetrahydro-5H-pyrido[2,3-d]azepine,
(5R)-4-chloro-N-ethyl-2-methoxy-5 -methyl-6,7,8,9-tetrahydro-5H-pyrido[2,3-d]azepin-3 -amine,
(5S)-4-chloro-N-ethyl-2-methoxy-5-methyl-6,7,8,9-tetrahydro-5H-pyrido[2,3-d]azepin-3-amine,
(5R)-3-bromo-4-chloro-2-methoxy-5-methyl-6,7,8,9-tetrahydro-5H-pyrido[2,3-d]azepine, and
(5S)-3-bromo-4-chloro-2-methoxy-5-methyl-6,7,8,9-tetrahydro-5H-pyrido[2,3-d]azepine,
and pharmaceutically acceptable salts thereof.

24. A compound according to claim 1, selected from:
2-Methoxy-8-methyl-5-methylene-7-(trifluoroacetyl)-6,7,8,9-tetrahydro-5H-pyrido[2,3-d]azepine,
2-methoxy-5,8-dimethyl-7-(trifluoroacetyl)-6,7,8,9-tetrahydro-5H-pyrido[2,3-d]azepine,
3-bromo-2-methoxy-5,8-dimethyl-7-(trifluoroacetyl)-6,7,8,9-tetrahydro-5H-pyrido[2,3-d]azepine,
2-methoxy-5-methylene-7-(trifluoroacetyl)-6,7,8,9-tetrahydro-5H-pyrido[2,3-d]azepine, 2-methoxy-5-methyl-7-(trifluoroacetyl)-6,7,8,9-tetrahydro-5H-pyrido[2,3-d]azepine,
5-methyl-7-(trifluoroacetyl)-6,7,8,9-tetrahydro-5H-pyrido[2,3-d]azepin-2-ol,
3-bromo-2-methoxy-5-methyl-7-(trifluoroacetyl)-6,7,8,9-tetrahydro-5H-pyrido[2,3-d]azepine,
3-chloro-2-methoxy-5-methyl-7-(trifluoroacetyl)-6,7,8,9-tetrahydro-5H-pyrido[2,3-d]azepine,
3-bromo-5-methyl-7-(trifluoroacetyl)-6,7,8,9-tetrahydro-5H-pyrido[2,3-d]azepin-2-ol,
3-iodo-5-methyl-7-(trifluoroacetyl)-6,7,8,9-tetrahydro-5H-pyrido[2,3-d]azepin-2-ol,
2-chloro-3-iodo-5-methyl-7-(trifluoroacetyl)-6,7,8,9-tetrahydro-5H-pyrido[2,3-d]azepine,
3-iodo-2-methoxy-5-methyl-7-(trifluoroacetyl)-6,7,8,9-tetrahydro-5H-pyrido[2,3-d]azepine,
2-(allyloxy)-3-iodo-5-methyl-7-(trifluoroacetyl)-6,7,8,9-tetrahydro-5H-pyrido[2,3-d]azepine,
2-chloro-5-methyl-7-(trifluoroacetyl)-6,7,8,9-tetrahydro-5H-pyrido[2,3-d]azepine,
3-bromo-2-chloro-5-methyl-7-(trifluoroacetyl)-6,7,8,9-tetrahydro-5H-pyrido[2,3-d]azepine,
2-methoxy-5-methyl-7-(trifluoroacetyl)-3-vinyl-6,7,8,9-tetrahydro-5H-pyrido[2,3-d]azepine,
3-ethyl-2-methoxy-5-methyl-7-(trifluoroacetyl)-6,7,8,9-tetrahydro-5H-pyrido[2,3-d]azepine,
2-(difluoromethoxy)-5-methyl-7-(trifluoroacetyl)-6,7,8,9-tetrahydro-5H-pyrido[2,3-d]azepine,
3-bromo-N,5-dimethyl-7-(trifluoroacetyl)-6,7,8,9-tetrahydro-5H-pyrido[2,3-d]azepin-2-amine,
2-methoxy-5-methyl-3-nitro-7-(trifluoroacetyl)-6,7,8,9-tetrahydro-5H-pyrido[2,3-d]azepine,
2-methoxy-5-methyl-7-(trifluoroacetyl)-6,7,8,9-tetrahydro-5H-pyrido[2,3-d]azepin-3-amine,
2-methoxy-N,N,5-trimethyl-7-(trifluoroacetyl)-6,7,8,9-tetrahydro-5H-pyrido[2,3-d]azepin-3-amine,
4-bromo-2-methoxy-5-methyl-7-(trifluoroacetyl)-6,7,8,9-tetrahydro-5H-pyrido[2,3-d]azepin-3-amine,
N-ethyl-2-methoxy-5-methyl-7-(trifluoroacetyl)-6,7,8,9-tetrahydro-5H-pyrido[2,3-d]azepin-3-amine,
4-chloro-N-ethyl-2-methoxy-5-methyl-7-(trifluoroacetyl)-6,7,8,9-tetrahydro-5H-pyrido[2,3-d]azepin-3-amine,
3,4-dibromo-2-methoxy-5-methyl-7-(trifluoroacetyl)-6,7,8,9-tetrahydro-5H-pyrido[2,3-d]azepine,
4-chloro-2-methoxy-5-methyl-7-(trifluoroacetyl)-6,7,8,9-tetrahydro-5H-pyrido[2,3-d]azepin-3-amine,
3-bromo-4-chloro-2-methoxy-5-methyl-7-(trifluoroacetyl)-6,7,8,9-tetrahydro-5H-pyrido[2,3-d]azepine,
3,4-dichloro-2-methoxy-5-methyl-7-(trifluoroacetyl)-6,7,8,9-tetrahydro-5H-pyrido[2,3-d]azepine,
5-methyl-3-nitro-7-(trifluoroacetyl)-6,7,8,9-tetrahydro-5H-pyrido[2,3-d]azepin-2-ol,
2-bromo-5-methyl-3-nitro-7-(trifluoroacetyl)-6,7,8,9-tetrahydro-5H-pyrido[2,3-d]azepine,
5-methyl-7-(trifluoroacetyl)-6,7,8,9-tetrahydro-5H-pyrido[2,3-d]azepin-3-amine,
3-bromo-5-methyl-7-(trifluoroacetyl)-6,7,8,9-tetrahydro-5H-pyrido[2,3-d]azepine,
7-tert-butyl 3-ethyl 4-hydroxy-2-oxo-1,2,5,6,8,9-hexahydro-7H-pyrido[2,3-d]azepine-3,7-dicarboxylate,
tert-butyl 4-hydroxy-2-oxo-1,2,5,6,8,9-hexahydro-7H-pyrido[2,3-d]azepine-7-carboxylate,
tert-butyl 3-bromo-4-hydroxy-2-oxo-1,2,5,6,8,9-hexahydro-7H-pyrido[2,3-d]azepine-7-carboxylate,
tert-butyl 3-bromo-4-hydroxy-2-methoxy-5,6,8,9-tetrahydro-7H-pyrido[2,3-d]azepine-7-carboxylate,
tert-butyl 2,4-dimethoxy-5,6,8,9-tetrahydro-7H-pyrido[2,3-d]azepine-7-carboxylate,
tert-butyl 4-hydroxy-2-methoxy-5,6,8,9-tetrahydro-7H-pyrido[2,3-d]azepine-7-carboxylate,
7-tert-butyl 3-ethyl 2,4-dimethoxy-5,6,8,9-tetrahydro-7H-pyrido[2,3-d]azepine-3,7-dicarboxylate,
7-tert-butyl 3-ethyl 4-hydroxy-9-methyl-2-oxo-1,2,5,6,8,9-hexahydro-7H-pyrido[2,3-d]azepine-3,7-dicarboxylate,
tert-butyl 4-hydroxy-9-methyl-2-oxo-1,2,5,6,8,9-hexahydro-7H-pyrido[2,3-d]azepine-7-carboxylate,
4-hydroxy-9-methyl-7-(trifluoroacetyl)-1,5,6,7,8,9-hexahydro-2H-pyrido[2,3-d]azepin-2-one,
4-bromo-9-methyl-7-(trifluoroacetyl)-1,5,6,7,8,9-hexahydro-2H-pyrido[2,3-d]azepin-2-one,
9-methyl-7-(trifluoroacetyl)-1,5,6,7,8,9-hexahydro-2H-pyrido[2,3-d]azepin-2-one,
2-bromo-9-methyl-7-(trifluoroacetyl)-6,7,8,9-tetrahydro-5H-pyrido[2,3-d]azepine,
and pharmaceutically acceptable salts thereof,
wherein if the compound exhibits chirality it can be in the form of a mixture of enantiomers or a mixture of diastereomers, or can be in the form of a single enantiomer or a single diastereomer.

25. A pharmaceutical composition comprising a compound of claim 1 and a pharmaceutically acceptable carrier.

26. A method of decreasing food intake of a patient comprising administering to said patient a pharmaceutically effective amount of a compound of claim 1.

27. A method of inducing satiety in a patient comprising administering to said patient a pharmaceutically effective amount of a compound of claim 1.

28. A method of controlling weight gain of a patient comprising administering to said patient a pharmaceutically effective amount of a compound of claim 1.

29. A method of treating obesity comprising administering to a patient in need of such treatment a pharmaceutically effective amount of a compound of claim 1.

* * * * *